US012805706B2

(12) United States Patent
Rothe et al.

(10) Patent No.: US 12,805,706 B2
(45) Date of Patent: Nov. 24, 2026

(54) CATHETER CONTROL SYSTEMS

(71) Applicant: INTUITIVE SURGICAL OPERATIONS, INC., Sunnyvale, CA (US)

(72) Inventors: Christopher A. Rothe, San Mateo, CA (US); Juan Diego Perea, Gilroy, CA (US); David Miller, Boulder, CO (US); Vahid Saadat, Atherton, CA (US); Zachary J. Malchano, San Francisco, CA (US); Ruey-Feng Peh, Singapore (SG)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 63 days.

(21) Appl. No.: 17/738,947

(22) Filed: May 6, 2022

(65) Prior Publication Data

US 2022/0280022 A1 Sep. 8, 2022

Related U.S. Application Data

(63) Continuation of application No. 14/795,325, filed on Jul. 9, 2015, now Pat. No. 11,350,815, which is a (Continued)

(51) Int. Cl.

| | |
|---|---|
| ***A61B 1/005*** | (2006.01) |
| ***A61M 25/00*** | (2006.01) |
| ***A61M 25/01*** | (2006.01) |

(52) U.S. Cl.

CPC .......... *A61B 1/0052* (2013.01); *A61B 1/0051* (2013.01); *A61B 1/0055* (2013.01); (Continued)

(58) Field of Classification Search

CPC ..... A61B 1/005; A61B 1/0051; A61B 1/0052; A61B 1/0053; A61B 1/0055; (Continued)

(56) References Cited

U.S. PATENT DOCUMENTS

| | | | |
|---|---|---|---|
| 623,022 | A | 4/1899 | Johnson |
| 2,305,462 | A | 12/1942 | Wolf |

(Continued)

FOREIGN PATENT DOCUMENTS

| | | | |
|---|---|---|---|
| DE | 10028155 | A1 | 12/2000 |
| EP | 0283661 | A2 | 9/1988 |

(Continued)

OTHER PUBLICATIONS

Avitall B., et al., "Right-Sided Driven Atrial Fibrillation in a Sterile Pericarditis Dog Model," Pacing and Clinical Electrophysiology, 1994, vol. 17, pp. 774.

(Continued)

*Primary Examiner* — Ryan N Henderson
(74) *Attorney, Agent, or Firm* — Haynes & Boone, LLP.

(57) ABSTRACT

A medical manipulation assembly includes a catheter and distal and proximal steering mechanisms. The catheter includes distal and proximal steerable portions with working channels configured to receive an instrument. The distal steering mechanism is operable to bend the distal steerable portion in a first plane relative to the proximal steerable portion in response to movement of a first portion of the distal steering mechanism about a first axis of rotation and to bend the distal steerable portion in a second plane relative to the proximal steerable portion in response to movement of a second portion of the distal steering mechanism about a second axis of rotation. The proximal steering mechanism is operable to bend the proximal steerable portion by rotational movement of the proximal steering mechanism. Distal pull- (Continued)

wires extend between the distal steerable portion and steering mechanism and proximal pullwires extend between the proximal steerable portion and steering mechanism.

20 Claims, 29 Drawing Sheets

Related U.S. Application Data continuation of application No. 12/499,011, filed on Jul. 7, 2009, now Pat. No. 9,101,735.

(60) Provisional application No. 61/078,746, filed on Jul. 7, 2008.

(52) U.S. Cl.
CPC .... *A61M 25/0082* (2013.01); *A61M 25/0105* (2013.01); *A61M 25/0136* (2013.01); *A61M 25/0147* (2013.01); *A61M 25/0074* (2013.01); *A61M 2025/015* (2013.01)

(58) Field of Classification Search
CPC ... A61B 1/0056; A61B 1/0057; A61B 1/0058; A61B 1/008; A61B 1/01; A61B 2017/003; A61B 2017/00305; A61B 2017/00309; A61B 2017/00314; A61B 2017/00318; A61B 2017/00323; A61B 2017/00327; A61B 2017/00331; A61M 25/0133; A61M 25/0136; A61M 25/0138; A61M 25/0141; A61M 25/0144; A61M 25/0147; A61M 25/0152; A61M 2025/015; A61M 2025/0161
See application file for complete search history.

(56) References Cited

U.S. PATENT DOCUMENTS 2,453,862 A 11/1948 Salisbury
3,557,780 A * 1/1971 Sato .................... A61B 1/0055 600/141
3,559,651 A 2/1971 David
3,788,303 A * 1/1974 Hall .................... A61B 1/0052 74/501.6
3,874,388 A 4/1975 King et al.
3,897,775 A * 8/1975 Furihata ............ A61B 1/00066 600/146
4,175,545 A 11/1979 Termanini
4,326,529 A 4/1982 Doss et al.
4,445,892 A 5/1984 Hussein et al.
4,470,407 A 9/1984 Hussein
4,517,976 A 5/1985 Murakoshi et al.
4,531,943 A * 7/1985 Van Tassel ......... A61M 25/1011 604/523
4,569,335 A 2/1986 Tsuno
4,576,146 A 3/1986 Kawazoe et al.
4,615,333 A 10/1986 Taguchi
4,619,247 A 10/1986 Inoue et al.
4,676,258 A 6/1987 Inokuchi et al.
4,681,093 A * 7/1987 Ono .................. A61B 1/00082 600/116
4,709,698 A 12/1987 Johnston et al.
4,710,192 A 12/1987 Liotta et al.
4,727,418 A 2/1988 Kato et al.
4,784,133 A * 11/1988 Mackin ............. A61B 1/00082 606/7
4,848,323 A 7/1989 Marijnissen et al.
4,873,965 A * 10/1989 Danieli ............. G02B 23/2476 600/152
4,911,148 A 3/1990 Sosnowski et al.
4,914,521 A 4/1990 Adair
4,943,290 A 7/1990 Rexroth et al.
4,950,285 A 8/1990 Wilk
4,957,484 A 9/1990 Murtfeldt
4,961,738 A * 10/1990 Mackin ................. A61B 1/018 600/116
4,976,710 A * 12/1990 Mackin ............... A61B 1/3137 604/917
4,991,578 A 2/1991 Cohen
4,994,069 A 2/1991 Ritchart et al.
4,998,916 A 3/1991 Hammerslag et al.
4,998,972 A 3/1991 Chin et al.
5,047,028 A 9/1991 Qian
5,057,106 A 10/1991 Kasevich et al.
5,060,632 A * 10/1991 Hibino ............... A61B 1/00042 600/109
5,090,959 A 2/1992 Samson et al.
5,123,428 A 6/1992 Schwarz
RE34,002 E 7/1992 Adair
5,156,141 A 10/1992 Krebs et al.
5,159,446 A * 10/1992 Hibino ............... A61B 1/00042 600/152
5,171,259 A 12/1992 Inoue
5,191,890 A * 3/1993 Hileman .............. A61B 8/4488 600/463
5,215,092 A * 6/1993 Wray .................... A61B 8/445 600/445
5,254,088 A * 10/1993 Lundquist ......... A61M 25/0136 604/95.04
5,281,238 A 1/1994 Chin et al.
5,282,827 A 2/1994 Kensey et al.
5,306,234 A 4/1994 Johnson
5,313,943 A 5/1994 Houser et al.
5,325,845 A * 7/1994 Adair .................. A61B 1/0055 604/95.04
5,330,496 A 7/1994 Alferness
5,334,159 A 8/1994 Turkel
5,334,193 A 8/1994 Nardella
5,336,252 A 8/1994 Cohen
5,339,800 A 8/1994 Wiita et al.
5,347,993 A * 9/1994 Tanaka ................ A61B 1/0057 600/109
5,348,554 A 9/1994 Imran et al.
5,352,237 A * 10/1994 Rodak ............... A61B 17/0218 606/205
5,353,792 A 10/1994 Luebbers et al.
5,370,647 A 12/1994 Graber et al.
5,373,840 A 12/1994 Knighton
5,375,612 A 12/1994 Cottenceau et al.
5,381,782 A * 1/1995 DeLaRama .......... A61B 1/0056 604/95.01
5,385,148 A 1/1995 Lesh et al.
5,391,182 A 2/1995 Chin
5,403,297 A * 4/1995 Imran ............... A61M 25/0158 600/434
5,403,326 A 4/1995 Harrison et al.
5,405,376 A 4/1995 Mulier et al.
5,413,107 A 5/1995 Oakley et al.
5,421,338 A 6/1995 Crowley et al.
5,431,649 A 7/1995 Mulier et al.
5,453,785 A 9/1995 Lenhardt et al.
5,462,521 A 10/1995 Brucker et al.
5,469,840 A * 11/1995 Tanii .................... A61B 1/0052 600/117
5,471,515 A 11/1995 Fossum et al.
5,487,757 A * 1/1996 Truckai ............ A61M 25/0144 604/95.04
5,498,230 A 3/1996 Adair
5,505,730 A 4/1996 Edwards
5,515,853 A 5/1996 Smith et al.
5,527,338 A 6/1996 Purdy
5,549,603 A 8/1996 Feiring
5,558,619 A 9/1996 Kami et al.
5,571,088 A 11/1996 Lennox et al.
5,575,756 A 11/1996 Karasawa et al.
5,575,810 A 11/1996 Swanson et al.
5,584,872 A 12/1996 Lafontaine et al.
5,591,119 A 1/1997 Adair
5,593,422 A 1/1997 Muijs et al.
5,593,424 A 1/1997 Northrup, III

(56) References Cited

U.S. PATENT DOCUMENTS

| | | | | | |
|---|---|---|---|---|---|
| 5,611,777 | A | * | 3/1997 | Bowden | A61M 25/0136 604/95.01 |
| 5,672,153 | A | | 9/1997 | Lax et al. | |
| 5,676,693 | A | | 10/1997 | Lafontaine | |
| 5,681,308 | A | | 10/1997 | Edwards et al. | |
| 5,695,448 | A | | 12/1997 | Kimura et al. | |
| 5,697,281 | A | | 12/1997 | Eggers et al. | |
| 5,697,882 | A | | 12/1997 | Eggers et al. | |
| 5,704,898 | A | | 1/1998 | Kokish | |
| 5,709,224 | A | | 1/1998 | Behl et al. | |
| 5,713,907 | A | | 2/1998 | Hogendijk et al. | |
| 5,713,946 | A | | 2/1998 | Ben-Haim | |
| 5,716,321 | A | | 2/1998 | Kerin et al. | |
| 5,722,403 | A | | 3/1998 | McGee et al. | |
| 5,725,523 | A | * | 3/1998 | Mueller | A61B 18/24 606/15 |
| 5,746,747 | A | | 5/1998 | McKeating | |
| 5,749,846 | A | | 5/1998 | Edwards et al. | |
| 5,749,890 | A | | 5/1998 | Shaknovich | |
| 5,754,313 | A | | 5/1998 | Pelchy et al. | |
| 5,766,137 | A | | 6/1998 | Omata | |
| 5,769,846 | A | | 6/1998 | Edwards et al. | |
| 5,792,045 | A | | 8/1998 | Adair | |
| 5,797,903 | A | | 8/1998 | Swanson et al. | |
| 5,823,947 | A | * | 10/1998 | Yoon | A61M 25/1011 600/207 |
| 5,823,955 | A | * | 10/1998 | Kuck | A61N 1/056 606/41 |
| 5,827,268 | A | | 10/1998 | Laufer | |
| 5,829,447 | A | | 11/1998 | Stevens et al. | |
| 5,842,973 | A | | 12/1998 | Bullard | |
| 5,843,118 | A | | 12/1998 | Sepetka et al. | |
| 5,848,969 | A | | 12/1998 | Panescu et al. | |
| 5,860,974 | A | | 1/1999 | Abele | |
| 5,860,991 | A | | 1/1999 | Klein et al. | |
| 5,865,791 | A | | 2/1999 | Whayne et al. | |
| 5,873,815 | A | | 2/1999 | Kerin et al. | |
| 5,879,366 | A | | 3/1999 | Shaw et al. | |
| 5,895,417 | A | | 4/1999 | Pomeranz et al. | |
| 5,897,487 | A | | 4/1999 | Ouchi | |
| 5,897,553 | A | | 4/1999 | Mulier et al. | |
| 5,902,328 | A | | 5/1999 | Lafontaine et al. | |
| 5,904,651 | A | | 5/1999 | Swanson et al. | |
| 5,908,445 | A | | 6/1999 | Whayne et al. | |
| 5,916,146 | A | * | 6/1999 | Allotta | A61B 1/0051 600/141 |
| 5,925,038 | A | | 7/1999 | Panescu et al. | |
| 5,928,250 | A | | 7/1999 | Koike et al. | |
| 5,929,901 | A | | 7/1999 | Adair et al. | |
| 5,935,102 | A | * | 8/1999 | Bowden | A61M 25/0147 604/95.04 |
| 5,938,616 | A | * | 8/1999 | Eaton | A61B 8/4466 600/463 |
| 5,941,845 | A | | 8/1999 | Tu et al. | |
| 5,944,690 | A | | 8/1999 | Falwell et al. | |
| 5,954,654 | A | * | 9/1999 | Eaton | A61M 25/0136 600/459 |
| 5,960,145 | A | * | 9/1999 | Sanchez | G02B 23/2469 385/115 |
| 5,964,740 | A | * | 10/1999 | Ouchi | A61M 25/0068 604/164.01 |
| 5,964,755 | A | | 10/1999 | Edwards | |
| 5,968,053 | A | | 10/1999 | Revelas | |
| 5,971,983 | A | | 10/1999 | Lesh | |
| 5,986,693 | A | | 11/1999 | Adair et al. | |
| 5,997,571 | A | | 12/1999 | Farr et al. | |
| 6,004,269 | A | | 12/1999 | Crowley et al. | |
| 6,012,457 | A | | 1/2000 | Lesh | |
| 6,024,740 | A | | 2/2000 | Lesh et al. | |
| 6,027,501 | A | | 2/2000 | Goble et al. | |
| 6,033,378 | A | * | 3/2000 | Lundquist | A61M 25/0147 604/95.01 |
| 6,036,685 | A | * | 3/2000 | Mueller | A61B 1/018 606/7 |
| 6,043,839 | A | | 3/2000 | Adair et al. | |
| 6,047,218 | A | | 4/2000 | Whayne et al. | |
| 6,063,077 | A | | 5/2000 | Schaer | |
| 6,063,081 | A | | 5/2000 | Mulier et al. | |
| 6,068,653 | A | | 5/2000 | Lafontaine | |
| 6,071,279 | A | | 6/2000 | Whayne et al. | |
| 6,071,302 | A | | 6/2000 | Sinofsky et al. | |
| 6,081,740 | A | | 6/2000 | Gombrich et al. | |
| 6,086,528 | A | | 7/2000 | Adair | |
| 6,086,534 | A | | 7/2000 | Kesten | |
| 6,099,498 | A | * | 8/2000 | Addis | A61M 1/3659 604/509 |
| 6,099,514 | A | | 8/2000 | Sharkey et al. | |
| 6,102,905 | A | | 8/2000 | Baxter et al. | |
| 6,112,123 | A | | 8/2000 | Kelleher et al. | |
| 6,115,626 | A | | 9/2000 | Whayne et al. | |
| 6,123,699 | A | | 9/2000 | Webster, Jr. | |
| 6,123,703 | A | | 9/2000 | Tu et al. | |
| 6,123,718 | A | | 9/2000 | Tu et al. | |
| 6,129,724 | A | | 10/2000 | Fleischman et al. | |
| 6,139,508 | A | | 10/2000 | Simpson et al. | |
| 6,142,993 | A | | 11/2000 | Whayne et al. | |
| 6,152,144 | A | | 11/2000 | Lesh et al. | |
| 6,156,350 | A | | 12/2000 | Constantz | |
| 6,159,203 | A | | 12/2000 | Sinofsky | |
| 6,161,543 | A | | 12/2000 | Cox et al. | |
| 6,164,283 | A | | 12/2000 | Lesh | |
| 6,167,297 | A | | 12/2000 | Benaron | |
| 6,168,591 | B1 | | 1/2001 | Sinofsky | |
| 6,168,594 | B1 | | 1/2001 | Lafontaine et al. | |
| 6,174,307 | B1 | | 1/2001 | Daniel et al. | |
| 6,178,346 | B1 | | 1/2001 | Amundson et al. | |
| 6,190,381 | B1 | | 2/2001 | Olsen et al. | |
| 6,211,904 | B1 | | 4/2001 | Adair et al. | |
| 6,224,553 | B1 | | 5/2001 | Nevo | |
| 6,231,561 | B1 | | 5/2001 | Frazier et al. | |
| 6,235,044 | B1 | | 5/2001 | Root et al. | |
| 6,237,605 | B1 | | 5/2001 | Vaska et al. | |
| 6,238,393 | B1 | | 5/2001 | Mulier et al. | |
| 6,240,312 | B1 | | 5/2001 | Alfano et al. | |
| 6,254,598 | B1 | | 7/2001 | Edwards et al. | |
| 6,258,083 | B1 | | 7/2001 | Daniel et al. | |
| 6,263,224 | B1 | | 7/2001 | West | |
| 6,270,492 | B1 | | 8/2001 | Sinofsky | |
| 6,275,255 | B1 | | 8/2001 | Adair et al. | |
| 6,290,689 | B1 | | 9/2001 | Delaney et al. | |
| 6,306,081 | B1 | * | 10/2001 | Ishikawa | A61B 1/018 600/116 |
| 6,310,642 | B1 | | 10/2001 | Adair et al. | |
| 6,311,692 | B1 | | 11/2001 | Vaska et al. | |
| 6,314,962 | B1 | | 11/2001 | Vaska et al. | |
| 6,314,963 | B1 | | 11/2001 | Vaska et al. | |
| 6,315,777 | B1 | | 11/2001 | Comben | |
| 6,315,778 | B1 | | 11/2001 | Gambale et al. | |
| 6,322,536 | B1 | | 11/2001 | Rosengart et al. | |
| 6,325,797 | B1 | | 12/2001 | Stewart et al. | |
| 6,328,727 | B1 | | 12/2001 | Frazier et al. | |
| 6,358,247 | B1 | | 3/2002 | Altman et al. | |
| 6,358,248 | B1 | | 3/2002 | Mulier et al. | |
| 6,375,654 | B1 | | 4/2002 | McIntyre | |
| 6,379,345 | B1 | | 4/2002 | Constantz | |
| 6,385,476 | B1 | | 5/2002 | Osadchy et al. | |
| 6,387,043 | B1 | | 5/2002 | Yoon | |
| 6,387,071 | B1 | | 5/2002 | Constantz | |
| 6,394,096 | B1 | | 5/2002 | Constantz | |
| 6,396,873 | B1 | | 5/2002 | Goldstein et al. | |
| 6,398,780 | B1 | | 6/2002 | Farley et al. | |
| 6,401,719 | B1 | | 6/2002 | Farley et al. | |
| 6,409,722 | B1 | | 6/2002 | Hoey et al. | |
| 6,416,511 | B1 | | 7/2002 | Lesh et al. | |
| 6,419,669 | B1 | | 7/2002 | Frazier et al. | |
| 6,423,051 | B1 | | 7/2002 | Kaplan et al. | |
| 6,423,055 | B1 | | 7/2002 | Farr et al. | |
| 6,423,058 | B1 | | 7/2002 | Edwards et al. | |
| 6,428,536 | B2 | | 8/2002 | Panescu et al. | |
| 6,436,118 | B1 | | 8/2002 | Kayan | |
| 6,440,061 | B1 | | 8/2002 | Wenner et al. | |
| 6,440,119 | B1 | | 8/2002 | Nakada et al. | |

(56) References Cited

U.S. PATENT DOCUMENTS 6,458,076 B1 * 10/2002 Pruitt .................. A61B 1/0051 600/128
6,458,151 B1 10/2002 Saltiel
6,464,697 B1 10/2002 Edwards et al.
6,474,340 B1 11/2002 Vaska et al.
6,475,223 B1 11/2002 Werp et al.
6,478,769 B1 11/2002 Parker
6,482,162 B1 11/2002 Moore
6,484,727 B1 11/2002 Vaska et al.
6,485,489 B2 11/2002 Teirstein et al.
6,488,671 B1 12/2002 Constantz et al.
6,494,902 B2 12/2002 Hoey et al.
6,497,705 B2 12/2002 Comben
6,500,174 B1 12/2002 Maguire et al.
6,502,576 B1 1/2003 Lesh
6,514,249 B1 2/2003 Maguire et al.
6,517,533 B1 2/2003 Swaminathan
6,527,979 B2 3/2003 Constantz et al.
6,532,380 B1 3/2003 Close et al.
6,533,767 B2 3/2003 Johansson et al.
6,537,272 B2 3/2003 Christopherson et al.
6,540,733 B2 4/2003 Constantz et al.
6,540,744 B2 4/2003 Hassett et al.
6,544,195 B2 4/2003 Wilson et al.
6,547,780 B1 4/2003 Sinofsky
6,558,375 B1 5/2003 Sinofsky et al.
6,558,382 B2 5/2003 Jahns et al.
6,562,020 B1 5/2003 Constantz et al.
6,572,609 B1 6/2003 Farr et al.
6,579,285 B2 6/2003 Sinofsky
6,585,732 B2 7/2003 Mulier et al.
6,587,709 B2 7/2003 Solf et al.
6,593,884 B1 7/2003 Gilboa et al.
6,605,055 B1 8/2003 Sinofsky et al.
6,613,062 B1 9/2003 Leckrone et al.
6,622,732 B2 9/2003 Constantz
6,626,855 B1 9/2003 Weng et al.
6,626,900 B1 9/2003 Sinofsky et al.
6,635,070 B2 10/2003 Leeflang et al.
6,645,202 B1 11/2003 Pless et al.
6,650,923 B1 11/2003 Lesh et al.
6,658,279 B2 12/2003 Swanson et al.
6,659,940 B2 12/2003 Adler
6,673,090 B2 1/2004 Root et al.
6,676,656 B2 1/2004 Sinofsky
6,679,836 B2 1/2004 Couvillon, Jr. et al.
6,682,526 B1 1/2004 Jones et al.
6,689,128 B2 2/2004 Sliwa et al.
6,692,430 B2 2/2004 Adler
6,701,581 B2 3/2004 Senovich et al.
6,701,931 B2 3/2004 Sliwa et al.
6,702,780 B1 3/2004 Gilboa et al.
6,704,043 B2 3/2004 Goldstein et al.
6,706,039 B2 3/2004 Mulier et al.
6,712,798 B2 3/2004 Constantz
6,719,747 B2 4/2004 Constantz et al.
6,719,755 B2 4/2004 Sliwa et al.
6,730,063 B2 5/2004 Delaney et al.
6,736,810 B2 5/2004 Hoey et al.
6,751,492 B2 6/2004 Ben-Haim
6,755,790 B2 6/2004 Stewart et al.
6,755,811 B1 6/2004 Constantz
6,764,487 B2 7/2004 Mulier et al.
6,771,996 B2 8/2004 Bowe et al.
6,773,402 B2 8/2004 Govari et al.
6,780,151 B2 * 8/2004 Grabover ............. A61B 1/0055 600/141
6,805,128 B1 10/2004 Pless et al.
6,805,129 B1 10/2004 Pless et al.
6,811,532 B2 * 11/2004 Ogura .................. A61B 1/0051 600/146
6,811,562 B1 11/2004 Pless
6,833,814 B2 12/2004 Gilboa et al.
6,837,849 B2 * 1/2005 Ogura .................. A61B 1/0055 600/146
6,840,923 B1 1/2005 Lapcevic
6,840,936 B2 1/2005 Sliwa et al.
6,849,073 B2 2/2005 Hoey et al.
6,858,005 B2 * 2/2005 Ohline ............... A61B 1/00057 600/141
6,858,026 B2 2/2005 Sliwa et al.
6,863,668 B2 3/2005 Gillespie et al.
6,866,651 B2 3/2005 Constantz
6,887,237 B2 5/2005 McGaffigan
6,892,091 B1 5/2005 Ben-Haim et al.
6,896,690 B1 5/2005 Lambrecht et al.
6,899,672 B2 5/2005 Chin et al.
6,899,673 B2 * 5/2005 Ogura .................. A61B 1/0051 600/146
6,915,154 B1 7/2005 Docherty et al.
6,916,284 B2 7/2005 Moriyama
6,923,805 B1 8/2005 Lafontaine et al.
6,926,669 B1 * 8/2005 Stewart ............. A61M 25/0147 601/3
6,929,010 B2 8/2005 Vaska et al.
6,932,809 B2 8/2005 Sinofsky
6,939,348 B2 9/2005 Malecki et al.
6,942,657 B2 9/2005 Sinofsky et al.
6,949,095 B2 9/2005 Vaska et al.
6,953,457 B2 10/2005 Farr et al.
6,955,173 B2 10/2005 Lesh
6,962,589 B2 11/2005 Mulier et al.
6,971,394 B2 12/2005 Sliwa et al.
6,974,464 B2 12/2005 Quijano et al.
6,979,290 B2 12/2005 Mourlas et al.
6,982,740 B2 1/2006 Adair et al.
6,984,232 B2 1/2006 Vanney et al.
6,994,094 B2 2/2006 Schwartz
7,019,610 B2 3/2006 Creighton et al.
7,025,746 B2 4/2006 Tal
7,030,904 B2 4/2006 Adair et al.
7,041,098 B2 5/2006 Farley et al.
7,042,487 B2 5/2006 Nakashima
7,044,135 B2 5/2006 Lesh
7,052,493 B2 5/2006 Vaska et al.
7,090,683 B2 8/2006 Brock et al.
7,112,195 B2 * 9/2006 Boll ....................... A61B 18/24 606/2
7,118,566 B2 10/2006 Jahns
7,156,845 B2 1/2007 Mulier et al.
7,163,534 B2 1/2007 Brucker et al.
7,166,537 B2 1/2007 Jacobsen et al.
7,169,144 B2 1/2007 Hoey et al.
7,186,214 B2 * 3/2007 Ness .................. A61B 17/3421 600/116
7,207,984 B2 4/2007 Farr et al.
7,217,268 B2 5/2007 Eggers et al.
7,242,832 B2 7/2007 Carlin et al.
7,247,155 B2 7/2007 Hoey et al.
7,261,711 B2 8/2007 Mulier et al.
7,263,397 B2 8/2007 Hauck et al.
7,276,061 B2 * 10/2007 Schaer ............... A61B 18/1492 607/99
7,309,328 B2 12/2007 Kaplan et al.
7,416,552 B2 8/2008 Paul et al.
7,435,248 B2 10/2008 Taimisto et al.
7,527,625 B2 5/2009 Knight et al.
7,534,204 B2 5/2009 Starksen et al.
7,569,052 B2 * 8/2009 Phan .................... A61B 18/082 606/35
7,678,117 B2 * 3/2010 Hinman ................. A61B 17/29 606/1
7,682,319 B2 * 3/2010 Martin ............... A61B 18/1492 604/165.01
7,736,347 B2 6/2010 Kaplan et al.
7,758,499 B2 7/2010 Adler
7,803,168 B2 * 9/2010 Gifford .............. A61B 18/1492 606/127
7,815,564 B2 * 10/2010 Geitz ................. A61B 1/00098 600/137
7,815,566 B2 * 10/2010 Stefanchik ......... A61B 1/00071 600/101
7,860,555 B2 12/2010 Saadat

(56) References Cited

U.S. PATENT DOCUMENTS 7,860,556 B2 12/2010 Saadat
7,988,619 B2 * 8/2011 Longo .................... A61B 1/32 606/198
8,052,607 B2 * 11/2011 Byrd .................... A61B 8/0883 600/459
8,131,350 B2 3/2012 Saadat et al.
8,137,333 B2 3/2012 Saadat et al.
8,206,287 B2 * 6/2012 Matsuo ................ A61B 1/0055 600/141
8,235,985 B2 8/2012 Saadat et al.
8,303,487 B2 * 11/2012 Ueno ................. A61B 1/00128 600/152
8,465,420 B2 * 6/2013 Ostrovsky ............ A61B 1/0057 600/141
8,657,805 B2 * 2/2014 Peh ...................... A61B 1/015 604/524
9,101,735 B2 8/2015 Rothe et al.
9,144,369 B2 * 9/2015 Ostrovsky ............ A61B 1/0057
9,668,641 B2 * 6/2017 Ostrovsky ............ A61B 1/0055
10,123,682 B2 * 11/2018 Ostrovsky .............. A61B 1/008
2001/0020126 A1 9/2001 Swanson et al.
2001/0039416 A1 11/2001 Moorman et al.
2001/0047136 A1 11/2001 Domanik et al.
2001/0047184 A1 11/2001 Connors
2002/0004644 A1 1/2002 Koblish
2002/0026145 A1 2/2002 Bagaoisan et al.
2002/0054852 A1 5/2002 Cate
2002/0058858 A1 * 5/2002 Ogura .................. A61B 1/0052 600/141
2002/0062063 A1 * 5/2002 Ogura .................. A61B 1/0051 600/141
2002/0065455 A1 5/2002 Ben-Haim et al.
2002/0087169 A1 7/2002 Brock et al.
2002/0091304 A1 * 7/2002 Ogura .................. A61B 1/0051 600/141
2002/0099266 A1 * 7/2002 Ogura .................. A61B 1/0055 600/139
2002/0138088 A1 9/2002 Nash et al.
2002/0165598 A1 11/2002 Wahr et al.
2002/0169377 A1 11/2002 Khairkhahan et al.
2003/0009085 A1 1/2003 Arai et al.
2003/0035156 A1 2/2003 Cooper
2003/0036698 A1 2/2003 Kohler et al.
2003/0069593 A1 4/2003 Tremulis et al.
2003/0120142 A1 6/2003 Dubuc et al.
2003/0130572 A1 7/2003 Phan et al.
2003/0144657 A1 7/2003 Bowe et al.
2003/0171741 A1 9/2003 Ziebol et al.
2003/0181939 A1 9/2003 Bonutti
2003/0208222 A1 11/2003 Zadno-Azizi
2003/0212394 A1 11/2003 Pearson et al.
2003/0220574 A1 11/2003 Markus et al.
2003/0222325 A1 12/2003 Jacobsen et al.
2004/0049211 A1 3/2004 Tremulis et al.
2004/0054335 A1 3/2004 Lesh et al.
2004/0054389 A1 3/2004 Osypka
2004/0059191 A1 * 3/2004 Krupa ............... A61M 25/0136 600/146
2004/0082833 A1 4/2004 Adler et al.
2004/0097788 A1 * 5/2004 Mourlas ................... A61B 1/05 600/116
2004/0106850 A1 * 6/2004 Yamaya ............. A61B 1/00098 600/107
2004/0117032 A1 6/2004 Roth
2004/0133113 A1 7/2004 Krishnan
2004/0138707 A1 7/2004 Greenhalgh
2004/0147806 A1 7/2004 Adler
2004/0147911 A1 7/2004 Sinofsky
2004/0147912 A1 7/2004 Sinofsky
2004/0147913 A1 7/2004 Sinofsky
2004/0158124 A1 * 8/2004 Okada .................... A61B 18/14 600/104
2004/0158143 A1 8/2004 Flaherty et al.
2004/0158289 A1 8/2004 Girouard et al.
2004/0167503 A1 8/2004 Sinofsky
2004/0181237 A1 9/2004 Forde et al.
2004/0199052 A1 10/2004 Banik et al.
2004/0210239 A1 10/2004 Nash et al.
2004/0215180 A1 10/2004 Starkebaum et al.
2004/0220471 A1 11/2004 Schwartz
2004/0230131 A1 11/2004 Kassab et al.
2004/0236316 A1 * 11/2004 Danitz ................... A61B 34/70 606/1
2004/0242960 A1 * 12/2004 Orban, III .............. A61B 10/06 600/106
2004/0242963 A1 * 12/2004 Matsumoto ........ G02B 23/2423 600/176
2004/0248837 A1 12/2004 Raz et al.
2004/0249367 A1 * 12/2004 Saadat ................. A61B 1/2736 600/101
2004/0254523 A1 12/2004 Fitzgerald et al.
2004/0260182 A1 12/2004 Zuluaga et al.
2005/0014995 A1 1/2005 Amundson et al.
2005/0015048 A1 1/2005 Chiu et al.
2005/0020914 A1 1/2005 Amundson et al.
2005/0027163 A1 2/2005 Chin et al.
2005/0038317 A1 * 2/2005 Ratnakar .............. A61B 1/0623 600/101
2005/0038419 A9 2/2005 Arnold et al.
2005/0059862 A1 * 3/2005 Phan .................. A61B 18/1482 600/128
2005/0059954 A1 3/2005 Constantz
2005/0059962 A1 * 3/2005 Phan .................... A61B 18/082 606/41
2005/0059965 A1 3/2005 Eberl et al.
2005/0065504 A1 3/2005 Melsky et al.
2005/0090709 A1 * 4/2005 Okada .................. A61B 17/072 600/153
2005/0090818 A1 4/2005 Pike et al.
2005/0096643 A1 5/2005 Brucker et al.
2005/0101984 A1 5/2005 Chanduszko et al.
2005/0107667 A1 * 5/2005 Danitz ................... A61B 34/70 600/139
2005/0107736 A1 5/2005 Landman et al.
2005/0119523 A1 * 6/2005 Starksen .......... A61B 17/00234 606/1
2005/0124969 A1 * 6/2005 Fitzgerald ............ A61B 5/0086 604/35
2005/0131401 A1 * 6/2005 Malecki ............. A61B 18/1492 606/27
2005/0154252 A1 7/2005 Sharkey et al.
2005/0159702 A1 7/2005 Sekiguchi et al.
2005/0165279 A1 7/2005 Adler et al.
2005/0165391 A1 7/2005 Maguire et al.
2005/0165466 A1 * 7/2005 Morris ............... A61B 17/3478 607/116
2005/0182465 A1 * 8/2005 Ness .................. A61B 17/3421 607/116
2005/0197530 A1 9/2005 Wallace et al.
2005/0197623 A1 9/2005 Leeflang et al.
2005/0215895 A1 9/2005 Popp et al.
2005/0222557 A1 10/2005 Baxter et al.
2005/0222558 A1 10/2005 Baxter et al.
2005/0228452 A1 10/2005 Mourlas et al.
2005/0234436 A1 10/2005 Baxter et al.
2005/0234437 A1 10/2005 Baxter et al.
2005/0267328 A1 12/2005 Blumzvig et al.
2005/0272975 A1 * 12/2005 McWeeney ............ A61B 1/307 600/172
2005/0272977 A1 * 12/2005 Saadat ............... A61B 1/00183 600/114
2005/0273085 A1 * 12/2005 Hinman ............... A61B 1/0055 606/1
2006/0009715 A1 1/2006 Khairkhahan et al.
2006/0009737 A1 1/2006 Whiting et al.
2006/0015096 A1 1/2006 Hauck et al.
2006/0022234 A1 2/2006 Adair et al.
2006/0025651 A1 2/2006 Adler et al.
2006/0025787 A1 2/2006 Morales et al.
2006/0041188 A1 * 2/2006 Dirusso ................ A61B 1/0055 600/152
2006/0069303 A1 3/2006 Couvillon, Jr.

(56) References Cited

U.S. PATENT DOCUMENTS

2006/0074398 A1 4/2006 Whiting et al.
2006/0084839 A1* 4/2006 Mourlas .................. A61B 1/05 600/116
2006/0084945 A1* 4/2006 Moll ...................... A61B 34/20 606/1
2006/0089637 A1 4/2006 Werneth et al.
2006/0094931 A1* 5/2006 Danitz .............. A61M 25/0138 606/1
2006/0111614 A1 5/2006 Saadat et al.
2006/0111615 A1 5/2006 Danitz et al.
2006/0122587 A1 6/2006 Sharareh
2006/0142694 A1* 6/2006 Bednarek ............... A61B 5/287 604/95.04
2006/0146172 A1 7/2006 Jacobsen et al.
2006/0149331 A1 7/2006 Mann et al.
2006/0155242 A1 7/2006 Constantz
2006/0161133 A1 7/2006 Laird et al.
2006/0167439 A1 7/2006 Kalser et al.
2006/0178560 A1* 8/2006 Saadat ................... A61B 17/29 600/141
2006/0183992 A1 8/2006 Kawashima et al.
2006/0200000 A1* 9/2006 Sato ..................... A61B 1/0057 600/146
2006/0217755 A1 9/2006 Eversull et al.
2006/0224167 A1 10/2006 Weisenburgh, II et al.
2006/0252993 A1* 11/2006 Freed .................. A61B 1/0052 604/95.04
2006/0253113 A1 11/2006 Arnold et al.
2006/0258909 A1 11/2006 Saadat et al.
2006/0271032 A1* 11/2006 Chin .................. A61B 18/1482 606/41
2007/0005019 A1 1/2007 Okishige
2007/0010708 A1* 1/2007 Ness .................. A61B 17/3421 600/114
2007/0015964 A1 1/2007 Eversull et al.
2007/0016130 A1 1/2007 Leeflang et al.
2007/0043338 A1 2/2007 Moll et al.
2007/0043413 A1 2/2007 Eversull et al.
2007/0049923 A1 3/2007 Jahns
2007/0055142 A1 3/2007 Webler
2007/0078451 A1 4/2007 Arnold et al.
2007/0083187 A1 4/2007 Eversull et al.
2007/0083217 A1 4/2007 Eversull et al.
2007/0093808 A1 4/2007 Mulier et al.
2007/0100324 A1 5/2007 Tempel et al.
2007/0106146 A1 5/2007 Altmann et al.
2007/0106214 A1 5/2007 Gray et al.
2007/0106287 A1 5/2007 O'Sullivan
2007/0135826 A1 6/2007 Zaver et al.
2007/0167801 A1 7/2007 Webler et al.
2007/0173694 A1* 7/2007 Tsuji .................... A61B 1/0052 600/118
2007/0249897 A1* 10/2007 Miyamoto ........... A61B 1/0055 600/104
2007/0260223 A1* 11/2007 Scheibe ............ A61M 25/0136 604/528
2007/0265609 A1 11/2007 Thapliyal et al.
2007/0265610 A1 11/2007 Thapliyal et al.
2007/0270686 A1 11/2007 Ritter et al.
2007/0282371 A1 12/2007 Lee et al.
2007/0287886 A1 12/2007 Saadat
2007/0293724 A1 12/2007 Saadat et al.
2008/0009747 A1 1/2008 Saadat et al.
2008/0009859 A1 1/2008 Auth et al.
2008/0015563 A1 1/2008 Hoey et al.
2008/0015569 A1 1/2008 Saadat et al.
2008/0021277 A1* 1/2008 Stefanchik ......... A61B 1/00154 600/127
2008/0027464 A1* 1/2008 Moll ...................... A61B 34/30 606/130
2008/0033241 A1 2/2008 Peh et al.
2008/0035701 A1 2/2008 Racenet et al.
2008/0039690 A1* 2/2008 Zubiate .............. A61B 1/00071 600/141
2008/0051631 A1* 2/2008 Dejima ............ A61B 17/00234 600/137
2008/0057106 A1 3/2008 Erickson et al.
2008/0058590 A1 3/2008 Saadat et al.
2008/0058650 A1 3/2008 Saadat et al.
2008/0058836 A1* 3/2008 Moll ................ A61B 17/12172 606/130
2008/0097476 A1 4/2008 Peh et al.
2008/0183081 A1 7/2008 Lys et al.
2008/0188759 A1 8/2008 Saadat et al.
2008/0208127 A1* 8/2008 Kuriyama .............. A61B 1/018 604/164.01
2008/0214889 A1 9/2008 Saadat et al.
2008/0214890 A1* 9/2008 Motai .................... A61B 1/018 600/107
2008/0228032 A1 9/2008 Starksen et al.
2008/0249356 A1 10/2008 Motai et al.
2008/0275300 A1 11/2008 Rothe et al.
2008/0287741 A1* 11/2008 Ostrovsky ......... A61M 25/0141 600/141
2008/0287790 A1 11/2008 Li
2008/0287805 A1 11/2008 Li
2008/0287961 A1* 11/2008 Miyamoto ............. A61B 1/018 606/127
2008/0300462 A1 12/2008 Intoccia et al.
2009/0030276 A1 1/2009 Saadat et al.
2009/0030412 A1 1/2009 Willis et al.
2009/0054803 A1 2/2009 Saadat et al.
2009/0062790 A1 3/2009 Malchano et al.
2009/0069694 A1* 3/2009 Amundson .............. A61B 8/12 600/467
2009/0076489 A1 3/2009 Welches et al.
2009/0082623 A1 3/2009 Rothe et al.
2009/0125022 A1 5/2009 Saadat et al.
2009/0137875 A1* 5/2009 Kitagawa ............. A61B 1/0055 600/146
2009/0143640 A1 6/2009 Saadat et al.
2009/0187074 A1 7/2009 Saadat et al.
2009/0203962 A1 8/2009 Miller et al.
2009/0221871 A1 9/2009 Peh et al.
2009/0227999 A1 9/2009 Willis et al.
2009/0264727 A1 10/2009 Markowitz et al.
2009/0264759 A1* 10/2009 Byrd ................. A61M 25/0136 600/445
2009/0267773 A1 10/2009 Markowitz et al.
2009/0275799 A1 11/2009 Saadat et al.
2009/0281524 A1* 11/2009 Scheibe ............ A61M 25/0136 604/528
2009/0287055 A1* 11/2009 Okamoto ............... A61B 1/009 600/152
2009/0299363 A1 12/2009 Saadat et al.
2009/0326572 A1 12/2009 Peh et al.
2010/0004506 A1 1/2010 Saadat
2010/0004661 A1 1/2010 Verin et al.
2010/0010311 A1 1/2010 Miller et al.
2010/0094081 A1 4/2010 Rothe et al.
2010/0130836 A1 5/2010 Malchano et al.
2011/0060227 A1 3/2011 Saadat
2011/0060298 A1 3/2011 Saadat
2011/0065990 A1* 3/2011 Verbeek ................. A61B 1/005 600/142
2011/0144576 A1 6/2011 Rothe et al.
2012/0016221 A1 1/2012 Saadat et al.
2012/0059366 A1 3/2012 Drews et al.
2012/0150046 A1 6/2012 Watson et al.
2013/0060239 A1* 3/2013 Hinman ................. A61B 17/29 606/1
2013/0261397 A1* 10/2013 Ostrovsky ......... A61M 25/0147 600/142
2014/0358088 A1* 12/2014 Miyamoto ......... A61B 17/3415 604/164.01
2015/0314107 A1 11/2015 Rothe et al.
2015/0359417 A1* 12/2015 Ostrovsky .......... A61B 1/00071 604/95.04

(56) References Cited

U.S. PATENT DOCUMENTS

2017/0231475 A1* 8/2017 McWeeney ............ A61B 1/008 600/109

FOREIGN PATENT DOCUMENTS

| | | | |
|---|---|---|---|
| EP | 0301288 | A1 | 2/1989 |
| JP | S5993413 | A | 5/1984 |
| JP | S59181315 | A | 10/1984 |
| JP | H01221133 | A | 9/1989 |
| JP | H03284265 | A | 12/1991 |
| JP | H05103746 | A | 4/1993 |
| JP | H0951897 | A | 2/1997 |
| JP | H11299725 | A | 11/1999 |
| JP | 2001258822 | A | 9/2001 |
| JP | 2007159738 | A * | 6/2007 |
| WO | WO-9221292 | A2 | 12/1992 |
| WO | WO-9407413 | A1 | 4/1994 |
| WO | WO-9503843 | A1 | 2/1995 |
| WO | WO-9818388 | A1 | 5/1998 |
| WO | WO-03039350 | A2 | 5/2003 |
| WO | WO-03053491 | A2 | 7/2003 |
| WO | WO-03101287 | A2 | 12/2003 |
| WO | WO-2004043272 | A1 | 5/2004 |
| WO | WO-2004080508 | A2 | 9/2004 |
| WO | WO-2005070330 | A1 | 8/2005 |
| WO | WO-2005077435 | A1 | 8/2005 |
| WO | WO-2005081202 | A1 | 9/2005 |
| WO | WO-2006017517 | A2 | 2/2006 |
| WO | WO-2006024015 | A1 | 3/2006 |
| WO | WO-2006083794 | A2 | 8/2006 |
| WO | WO-2006091597 | A1 | 8/2006 |
| WO | WO-2006126979 | A2 | 11/2006 |
| WO | WO-2007067323 | A2 | 6/2007 |
| WO | WO-2007079268 | A2 | 7/2007 |
| WO | WO-2007133845 | A2 | 11/2007 |
| WO | WO-2007134258 | A2 | 11/2007 |
| WO | WO-2008015625 | A2 | 2/2008 |
| WO | WO-2008021994 | A2 | 2/2008 |
| WO | WO-2008021997 | A2 | 2/2008 |
| WO | WO-2008021998 | A2 | 2/2008 |
| WO | WO-2008024261 | A2 | 2/2008 |
| WO | WO-2008079828 | A2 | 7/2008 |
| WO | WO-2009112262 | A2 | 9/2009 |

OTHER PUBLICATIONS

Avitall, et al. "A Catheter System to Ablate Atrial Fibrillation in a Sterile Pericarditis Dog Model," Pacing and Clinical Electrophysiology, 1994, vol. 17, pp. 774.

Avitall, "Vagally Mediated Atrial Fibrillation in a Dog Model can be Ablated by Placing Linear Radiofrequency Lesions at the Junction of the Right Atrial Appendage and the Superior Vena Cava," Pacing and Clinical Electrophysiology, 1995, vol. 18, pp. 857.

Baker B.M., et al., "Nonpharmacologic Approaches to the Treatment of Atrial Fibrillation and Atrial Flutter," Journal of Cardiovascular Electrophysiology, 1995, vol. 6 (10 Pt 2), pp. 972-978.

Bhakta D., et al., "Principles of Electroanatomic Mapping," Indian Pacing and Electrophysiology Journal, 2008, vol. 8 (1), pp. 32-50.

Bidoggia H., et al., "Transseptal Left Heart Catheterization: Usefulness of the Intracavitary Electrocardiogram in the Localization of the Fossa Ovalis," Cathet Cardiovasc Diagn, 1991, vol. 24 (3), pp. 221-225, PMID: 1764747 [online], [retrieved Feb. 15, 2010]. Retrieved from the Internet: URL: http://www.ncbi.nlm.nih.gov/sites/entrez.

Bredikis J.J., et al., "Surgery of Tachyarrhythmia: Intracardiac Closed Heart Cryoablation," Pacing and Clinical Electrophysiology, 1990, vol. 13 (Part 2), pp. 1980-1984.

Communication from the Examining Division for Application No. EP06734083.6 mailed on Nov. 12, 2010, 3 pages.

Communication from the Examining Division for Application No. EP06734083.6 mailed on Oct. 23, 2009, 1 page.

Communication from the Examining Division for Application No. EP08746822.9 mailed on Jul. 13, 2010, 1 page.

Cox J.L., "Cardiac Surgery for Arrhythmias," Journal of Cardiovascular Electrophysiology, 2004, vol. 15, pp. 250-262.

Cox J.L., et al., "Five-Year Experience With the Maze Procedure for Atrial Fibrillation," The Annals of Thoracic Surgery, 1993, vol. 56, pp. 814-824.

Cox J.L., et al., "Modification of the Maze Procedure for Atrial Flutter and Atrial Fibrillation," The Journal of Thoracic and Cardiovascular Surgery, 1995, vol. 110, pp. 473-484.

Cox J.L., "The Status of Surgery for Cardiac Arrhythmias," Circulation, 1985, vol. 71, pp. 413-417.

Cox J.L., "The Surgical Treatment of Atrial Fibrillation," The Journal of Thoracic and Cardiovascular Surgery, 1991, vol. 101, pp. 584-592.

Elvan A., et al., "Radiofrequency Catheter Ablation of the Atria Reduces Inducibility and Duration of Atrial Fibrillation in Dogs," Circulation, vol. 91, 1995, pp. 2235-2244 [online], [retrieved Feb. 4, 2013]. Retrieved from the Internet: URL: http://circ.ahajournals.org/cgi/content/full/91/8/2235.

Elvan A., et al., "Radiofrequency Catheter Ablation (RFCA) of the Atria Effectively Abolishes Pacing Induced Chronic Atrial Fibrillation," Pacing and Clinical Electrophysiology, 1995, vol. 18, pp. 856.

Elvan, et al., "Replication of the 'Maze' Procedure by Radiofrequency Catheter Ablation Reduces the Ability to Induce Atrial Fibrillation," Pacing and Clinical Electrophysiology, 1994, vol. 17, pp. 774.

European Search Report for Application No. EP07799466.3 mailed on Nov. 18, 2010, 9 pages.

European Search Report for Application No. EP08746822.9 mailed on Mar. 29, 2010, 7 Pages.

Examination Communication for Application No. EP06734083.6 mailed on May 18, 2010, 3 Pages.

Extended European Search Report for Application No. EP06734083.6 mailed on Jul. 1, 2009, 6 pages.

Fieguth H.G., et al., "Inhibition of Atrial Fibrillation by Pulmonary Vein Isolation and Auricular Resection—Experimental Study in a Sheep Model," The European Journal of Cardio-Thoracic Surgery, 1997, vol. 11, pp. 714-721.

Final Office Action mailed Mar. 1, 2010 for U.S. Appl. No. 12/117,655, filed May 8, 2008.

Final Office Action mailed Jun. 2, 2011 for U.S. Appl. No. 12/117,655, filed May 8, 2008.

Final Office Action mailed May 12, 2011 for U.S. Appl. No. 11/775,771, filed Jul. 10, 2007.

Final Office Action mailed Sep. 16, 2010 for U.S. Appl. No. 11/828,267, filed Jul. 25, 2007.

Hoey M.F., et al., "Intramural Ablation Using Radiofrequency Energy via Screw-Tip Catheter and Saline Electrode," Pacing and Clinical Electrophysiology, 1995, vol. 18, Part II, 487.

Huang, "Increase in the Lesion Size and Decrease in the Impedance Rise with a Saline Infusion Electrode Catheter for Radiofrequency," Circulation, 1989, vol. 80 (4), II-324.

Moser K.M ., et al., "Angioscopic Visualization of Pulmonary Emboli," Chest, 1980, vol. 77 (2), pp. 198-201.

Nakamura F., et al., "Percutaneous Intracardiac Surgery With Cardioscopic Guidance," SPIE, 1992, vol. 1642, pp. 214-216.

Non-Final Office Action mailed Jun. 7, 2011 for U.S. Appl. No. 12/323,281, filed Nov. 25, 2008.

Non-Final Office Action mailed Jun. 8, 2009 for U.S. Appl. No. 12/117,655, filed May 8, 2008 (VYMD02000/US).

Non-Final Office Action mailed May 9, 2011 for U.S. Appl. No. 11/961,950, filed Dec. 20, 2007 (VYMD01500/US).

Non-Final Office Action mailed May 9, 2011 for U.S. Appl. No. 11/961,995, filed Dec. 20, 2007 (VYMD01600/US).

Non-Final Office Action mailed May 9, 2011 for U.S. Appl. No. 11/962,029, filed Dec. 20, 2007 (VYMD02900/US).

Non-Final Office Action mailed Jun. 10, 2010 for U.S. Appl. No. 11/560,742, filed Nov. 16, 2006 (VYMD01300/US).

Non-Final Office Action mailed Apr. 11, 2011 for U.S. Appl. No. 11/763,399, filed Jun. 14, 2007 (VYMD00400/US).

Non-Final Office Action mailed Mar. 11, 2011 for U.S. Appl. No. 11/848,202, filed Aug. 30, 2007 (VYMD00900/US).

Non-Final Office Action mailed May 11, 2011 for U.S. Appl. No. 11/828,267, filed Jul. 25, 2007 (VYMD00800/US).

(56) References Cited

OTHER PUBLICATIONS

Non-Final Office Action mailed Jan. 14, 2010 for U.S. Appl. No. 11/828,267, filed Jul. 25, 2007 (VYMD00800/US).
Non-Final Office Action mailed Dec. 16, 2010 for U.S. Appl. No. 12/117,655, filed May 8, 2008 (VYMD02000/US).
Non-Final Office Action mailed Feb. 18, 2011 for U.S. Appl. No. 12/947,198, filed Nov. 16, 2010.
Non-Final Office Action mailed Feb. 18, 2011 for U.S. Appl. No. 12/947,246, filed Nov. 16, 2006.
Non-Final Office Action mailed May 20, 2011 for U.S. Appl. No. 11/775,819, filed Jul. 10, 2007.
Non-Final Office Action mailed May 20, 2011 for U.S. Appl. No. 11/877,386, filed Oct. 23, 2007 (VYMD01200/US).
Non-Final Office Action mailed Jul. 21, 2010 for U.S. Appl. No. 11/687,597, filed Mar. 16, 2007 (VYMD00300/US).
Non-Final Office Action mailed Apr. 22, 2011 for U.S. Appl. No. 12/367,019, filed Feb. 6, 2009 (VYMD03000/US).
Non-Final Office Action mailed May 23, 2011 for U.S. Appl. No. 11/775,837, filed Jul. 10, 2007.
Non-Final Office Action mailed Nov. 24, 2010 for U.S. Appl. No. 11/848,429, filed Aug. 31, 2007 (VYMD01000/US).
Non-Final Office Action mailed Nov. 24, 2010 for U.S. Appl. No. 12/464,800, filed May 12, 2009 (VYMD01000C1/US).
Non-Final Office Action mailed Apr. 25, 2011 for U.S. Appl. No. 11/959,158, filed Dec. 18, 2007 (VYMD01400/US).
Non-Final Office Action mailed Feb. 25, 2010 for U.S. Appl. No. 11/259,498, filed Oct. 25, 2005 (VYMDN0200/US).
Non-Final Office Action mailed Feb. 25, 2011 for U.S. Appl. No. 11/848,207, filed Aug. 30, 2007 (VYMD01100/US).
Non-Final Office Action mailed Apr. 26, 2011 for U.S. Appl. No. 11/848,532, filed Aug. 31, 2007.
Non-Final Office Action mailed Apr. 27, 2011 for U.S. Appl. No. 11/828,281, filed Jul. 25, 2007.
Non-Final Office Action mailed Aug. 27, 2010 for U.S. Appl. No. 11/775,771, filed Jul. 10, 2007 (VYMD00700/US).
Non-Final Office Action mailed Dec. 27, 2010 for U.S. Appl. No. 12/026,455, filed Feb. 5, 2008 (VYMD01700/US).
Notice of Allowance mailed Feb. 3, 2011 for U.S. Appl. No. 11/560,732, filed Nov. 16, 2006 (VYMD00100/US).
Notice of Allowance mailed Jun. 13, 2011 for Japanese Application No. 2007-554156 filed Jan. 30, 2006.
Notice of Allowance mailed Nov. 15, 2010 for U.S. Appl. No. 11/259,498, filed Oct. 25, 2005 (VYMDN0200/US).
Notice of Allowance mailed Nov. 15, 2010 for U.S. Appl. No. 11/560,742, filed Nov. 16, 2006 (VYMD01300/US).
Notice of Allowance mailed Feb. 24, 2011 for U.S. Appl. No. 11/560,732, filed Mar. 16, 2007 (VYMD00100/US).
Notice of Allowance mailed Feb. 24, 2011 for U.S. Appl. No. 11/687,597, filed Mar. 16, 2007 (VYMD00300/US).
Office Action mailed Feb. 15, 2011 for Japanese Application No. 2007-554156 filed Jan. 30, 2006.
Office Action mailed Apr. 27, 2011 for Japanese Application No. 2009-500630 filed Mar. 16, 2007.
Pappone C., et al., "Circumferential Radiofrequency Ablation of Pulmonary Vein Ostia," Circulation, 2000, vol. 102, pp. 2619-2628.
Sethi K.K., et al., "Transseptal catheterization for the electrophysiologist: modification with a 'view'," Journal of Interventional Cardiac Electrophysiology, 2001, vol. 5 (1), pp. 97-99.
Supplemental European Search Report for Application No. EP07758716 mailed on Feb. 28, 2011, 8 Pages.
Supplementary European search report for Application No. EP07812146.4 mailed on Nov. 18, 2010, 8 Pages.
Supplementary European Search Report for Application No. EP07841754, mailed on Jun. 30, 2010, 6 pages (VYMD02400/EP).
Thiagalingam A., et al., "Cooled Needle Catheter Ablation Creates Deeper and Wider Lesions than Irrigated Tip Catheter Ablation," Journal of Cardiovascular Electrophysiology, 2005, vol. 16 (5), pp. 1-8.
Uchida Y., "Developmental History of Cardioscopes", in: Coronary Angioscopy, Chapter 19, Futura Publishing Company, Inc., 2001, pp. 187-197.
U.S. Appl. No. 61/286,283, inventor Rothe; Chris A., filed Dec. 14, 2009.
U.S. Appl. No. 61/297,462, inventor Rothe; Chris A., filed Jan. 22, 2010.
Willkampf F.H., et al., "Radiofrequency Ablation with a Cooled Porous Electrode Catheter," JACC, Abstract, 1988, vol. 11 (2), pp. 17A.

* cited by examiner

CATHETER CONTROL SYSTEMS

CROSS-REFERENCE TO RELATED APPLICATIONS

This application is a continuation of U.S. patent application Ser. No. 14/795,325 filed Jul. 9, 2015, which is the continuation U.S. patent application Ser. No. 12/499,011, filed Jul. 7, 2009, which claims the benefit of priority to U.S. Prov. Pat. App. 61/078,746, entitled, "CATHETER CONTROL SYSTEMS", filed Jul. 7, 2008, which are incorporated herein by reference in their entirety.

FIELD OF THE INVENTION

The present invention relates generally to catheter control systems for controlling the articulation of visualization and treatment apparatus having imaging and manipulation features for intravascularly accessing regions of the body.

BACKGROUND OF THE INVENTION

Conventional devices for accessing and visualizing interior regions of a body lumen are known. For example, various catheter devices are typically advanced within a patient's body, e.g., intravascularly, and advanced into a desirable position within the body. Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, many of the conventional catheter imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. Nos. 5,895,417; 5,941,845; and 6,129,724, used on the epicardial surface of the heart may be difficult in assuring a transmural lesion or complete blockage of electrical signals. In addition, current devices may have difficulty dealing with varying thickness of tissue through which a transmural lesion is desired.

Conventional accompanying imaging devices, such as fluoroscopy, are unable to detect perpendicular electrode orientation, catheter movement during the cardiac cycle, and image catheter position throughout lesion formation. The absence of real-time visualization also poses the risk of incorrect placement and ablation of structures such as sinus node tissue which can lead to fatal consequences.

Moreover, because of the tortuous nature of intravascular access, devices or mechanisms at the distal end of a catheter positioned within the patient's body, e.g., within a chamber of the heart, are typically no longer aligned with the handle. Steering or manipulation of the distal end of the catheter via control or articulation mechanisms on the handle is easily disorienting to the user as manipulation of a control on the handle in a first direction may articulate the catheter distal end in an unexpected direction depending upon the resulting catheter configuration leaving the user to adjust accordingly. However, this results in reduced efficiency and longer procedure times as well as increased risks to the patient. Accordingly, there is a need for improved catheter control systems which facilitate the manipulation and articulation of a catheter.

BRIEF SUMMARY OF THE INVENTION

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

In an exemplary variation for imaging tissue surfaces within a heart chamber containing blood, the tissue imaging and treatment system may generally comprise a catheter body having a lumen defined therethrough, a visualization element disposed adjacent the catheter body, the visualization element having a field of view, a transparent fluid source in fluid communication with the lumen, and a barrier or membrane extendable from the catheter body to localize, between the visualization element and the field of view, displacement of blood by transparent fluid that flows from the lumen, and an instrument translatable through the displaced blood for performing any number of treatments upon the tissue surface within the field of view. The imaging hood may be formed into any number of configurations and the imaging assembly may also be utilized with any number of therapeutic tools which may be deployed through the deployment catheter.

More particularly in certain variations, the tissue visualization system may comprise components including the imaging hood, where the hood may further include a membrane having a main aperture and additional optional openings disposed over the distal end of the hood. An introducer sheath or the deployment catheter upon which the imaging hood is disposed may further comprise a steerable segment made of multiple adjacent links which are pivotably connected to one another and which may be articulated within a single plane or multiple planes. The deployment catheter itself may be comprised of a multiple lumen extrusion, such as a four-lumen catheter extrusion, which is reinforced with braided stainless steel fibers to provide structural support. The proximal end of the catheter may be coupled to a handle for manipulation and articulation of the system.

To provide visualization, an imaging element such as a fiberscope or electronic imager such as a solid state camera, e.g., CCD or CMOS, may be mounted, e.g., on a shape memory wire, and positioned within or along the hood interior. A fluid reservoir and/or pump (e.g., syringe, pressurized intravenous bag, etc.) may be fluidly coupled to the proximal end of the catheter to hold the translucent fluid such as saline or contrast medium as well as for providing the pressure to inject the fluid into the imaging hood.

One example of a system configured to enable direct visualization of tissue underlying the hood and optionally treat tissue, e.g., ablation, may include an ablation assembly, hood, and deployment catheter coupled to a handle having a catheter steering and locking assembly integrated along the handle. The catheter steering and locking assembly may include a steering member pivotably coupled to a locking member where the steering member may be coupled to one or more pullwires attached thereto via a retaining member, e.g., set screw, such that manipulation of the steering member articulates the steerable section and hood in a corresponding manner. The steering member may be pivotably coupled to the locking member along a point of rotation and locking mechanism which is attached to a steering plate.

The catheter shaft contains at least one lumen which allows the passage of one or more pullwires that are connected to the steering member at the proximal end of the pullwire while the distal end may be terminated and anchored to the steering mechanisms along the steerable portion of the catheter. A compression coil, e.g., made of stainless steel, with a slightly larger diameter than the pullwire may be positioned about the pullwire within the handle to allow the pullwire to slide freely therethrough.

In use, the steering member may be actuated, e.g., by pulling the member proximally, to articulate the steerable portion and hood in the same direction of articulation. With the steerable portion articulated to the degree desired to position the hood, the locking member may be actuated to maintain a configuration of the steerable portion and hood by preventing or inhibiting movement of the steering member thus freeing the hand or hands of the user. A steering indicator and/or locking indicator may be optionally incorporated along the handle as a reminder to the user.

The handle assembly may also optionally incorporate an optical adjustment assembly which may be used to move the distal lens of a visualization instrument, such as a fiberscope, distally or proximally from the imaged tissue region, hence simulating a zoom-in and/or zoom-out optical effect. Generally, the optical adjustment assembly is able to provide zoom-in and/or zoom-out capabilities by varying the length of the assembly. By rotating an adjustment member, which is coupled to a retaining sleeve within the optical adjustment assembly, a distal shaft portion may be advanced or retracted relative to the guide shaft. The assembly may be accordingly varied in length while distally or proximally advancing the fiberscope based on the varied length of the optical adjustment assembly to control the visualized field of view.

Because manipulation of the hood and steerable portion corresponds with an angle at which the handle is positioned, the handle may also serve as an orientation indicator for the hood and steerable portion once the hood has been introduced into the patient's body. This correspondence between the planes of the handle and the resulting articulation of the hood and steerable portion may be particularly useful for efficiently controlling the hood position within the patient's body. As the catheter is usually repeatedly torqued during a procedure, keeping track of the orientation of the deflection of the hood can be difficult, if not impossible, unless fluoroscopy is used. With the handle, the angle of deflection of the hood can be predicted by the operator without the need of fluoroscopy. This is can be particularly desirable in procedures such as transseptal punctures where an accurate angle of puncture of the septal wall is desirable to avoid complications such as perforation of the aorta.

Another variation of a steering handle assembly may include an assembly having a handle portion and a steering ring which may be manipulated along any number of directions relative to the housing to control the articulation of the hood. Manipulating or pulling along a portion of the steering ring causes the steerable portion and hood to move along a corresponding direction of articulation. Moreover, because of the manner in which the steering ring is positioned to encircle the handle assembly, the operator may grip the handle along any orientation and operate the handle assembly with a single hand.

The handle assembly may generally comprise a ball pivot supported by pivot support enclosed within the housing. The ball pivot may support the steering ring via one or more steering ring support members, e.g., four steering ring support members, which extend radially through corresponding support member openings. Because of the ball pivot shape, the steering ring may be moved about the pivot in any number of directions. The terminal ends of one or more pullwires may be coupled the steering ring via corresponding fasteners, e.g., set screws, securing each of the pullwire termination crimps. These pullwires may extend through the pivot support housing and through a pullwire transition manifold and into a proximal end of a multi-lumen shaft, such as the catheter. The pullwires may continue distally through the catheter where they are coupled to the steerable portion of the catheter. Each of the pullwires may be optionally encased in corresponding compression coils between the transition manifold and catheter.

Although multiple pullwires may be utilized depending upon the number of directions for articulation, four pullwires may be typically utilized. Each of the four pullwires may be terminated symmetrically around a circumference of the steering ring such that a balanced four-way steering of the distal portion may be accomplished, although manipulating the steering ring along various portions of its circumference may yield combinational articulation between the pullwires to result in numerous catheter configurations. Additionally, the handle assembly may further incorporate a spring mechanism as an overdrive prevention mechanism positioned between the transition manifold and ball pivot in order to prevent over-tensioning or breaking of the pullwires if the steering ring is over-deflected in a direction.

The handle assembly and catheter can be consistently deflected in the same direction by which the steering ring is being deflected regardless of the orientation of the handle assembly. For example, the handle assembly may be deflected in a first direction of actuation such that the hood is deflected in a corresponding first direction of articulation. If the handle assembly, catheter, and hood are then rotated along an arbitrary direction of rotation about the longitudinal axis of the assembly, even with the entire assembly rotated, e.g., 180°, actuating the steering ring along the first direction of actuation still results in a corresponding first direction of articulation of the hood which matches the initial direction of articulation despite the rotated assembly.

In yet another variation of the catheter control handle, the control assembly may be configured to articulate at least two independently deflectable portions. As with previous variations, a steering ring may encircle the housing. However, this variation further includes a proximal handle portion extending from the housing with a proximal section control for articulating the proximal steerable section. Moreover, this particular handle assembly may be used to control articulation of the hood and the distal steerable section but also used to further control articulation of the proximal steerable section. A proximal section control located along the proximal handle portion may be actuated, e.g., by rotating the control in a first and/or second direction, to articulate the proximal steerable section within a first plane and the hood may be further articulated by manipulating the steering ring such that distal steerable section moves in a corresponding direction of articulation.

Additionally and/or alternatively, visual indicators positioned directly upon the hood may also be utilized in coordination with corresponding visual indicators positioned upon the handle itself. The hood may have one or more visual indicators marked upon the distal portion of the hood such that the visual image through the hood may show at least a first directional indicator along a first portion of the hood. The handle assembly may thus have one or more directional indicators located directly upon, e.g., the steering ring, which correspond spatially with the indicators positioned upon the hood or hood membrane.

The catheter control systems described herein may additionally integrate any number of features and controls for facilitate procedures. These features and controls may be integrated into any of the variations described herein. One example may include features such as flow rate control, air bubble detection, ablation activation switches, built-in image sensors, etc., may be incorporated into the handle assembly.

DETAILED DESCRIPTION OF THE INVENTION

A tissue-imaging and manipulation apparatus described herein is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
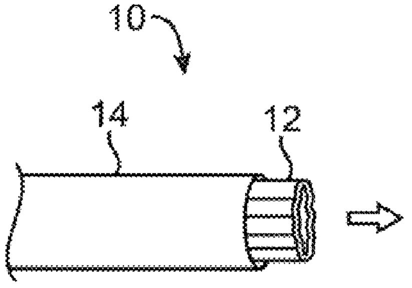
FIG. 1A shows a side view of one variation of a tissue imaging apparatus during deployment from a sheath or delivery catheter.
Figure 1B:
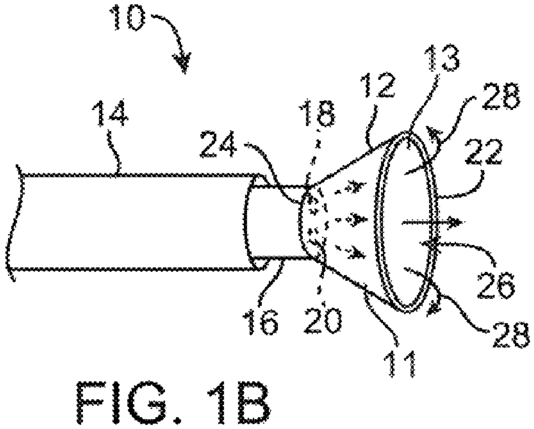
FIG. 1B shows the deployed tissue imaging apparatus of FIG. 1A having an optionally expandable hood or sheath attached to an imaging and/or diagnostic catheter.
Figure 1C:
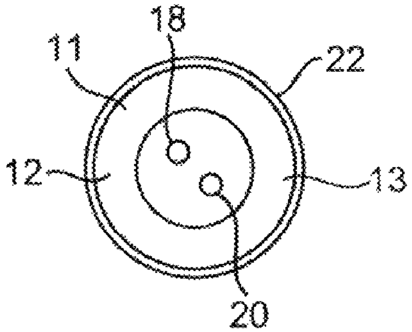
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, DE), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
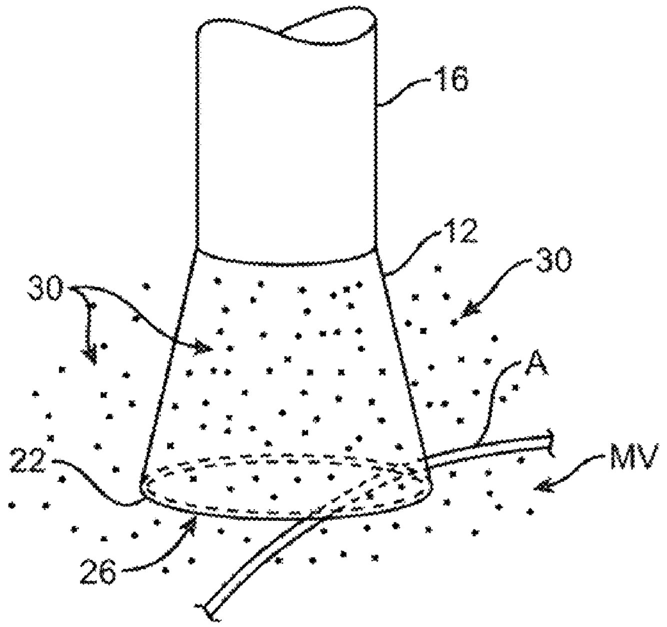
FIGS. 2A and 2B show one example of a deployed tissue imager positioned against or adjacent to the tissue to be imaged and a flow of fluid, such as saline, displacing blood from within the expandable hood.
Figure 2B:
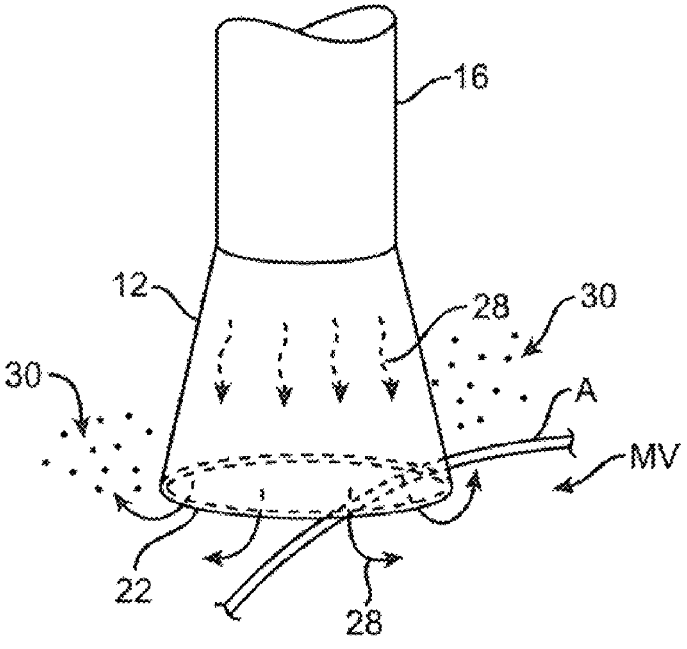

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
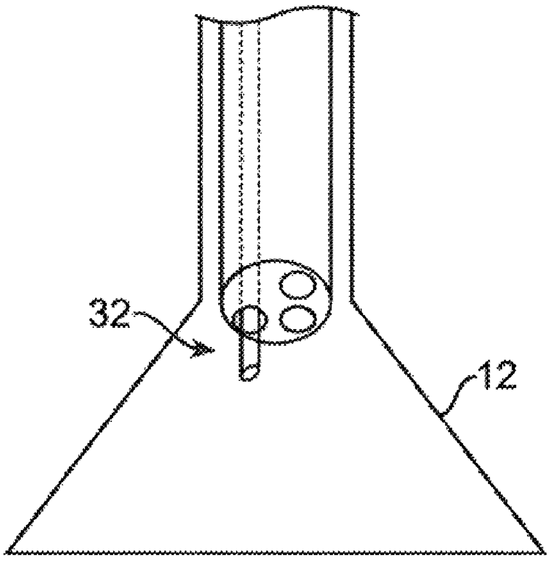
FIGS. 3A and 3B show examples of various visualization imagers which may be utilized within or along the imaging hood.
Figure 3B:
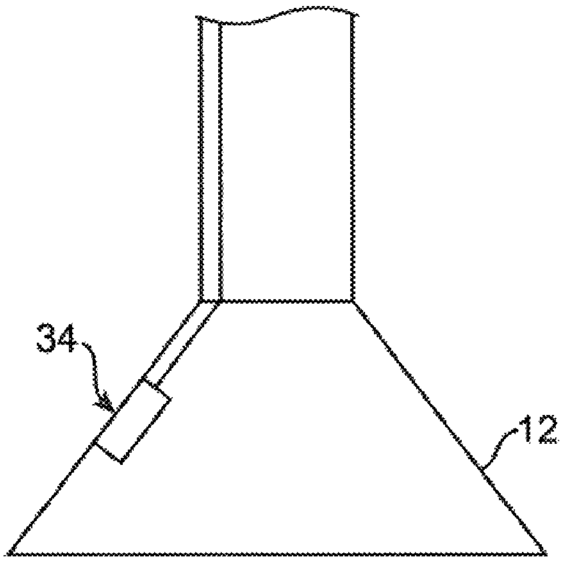

FIG. 3A shows a partial cross-sectional view of an example where one or more optical fiber bundles 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

Figure 4A:
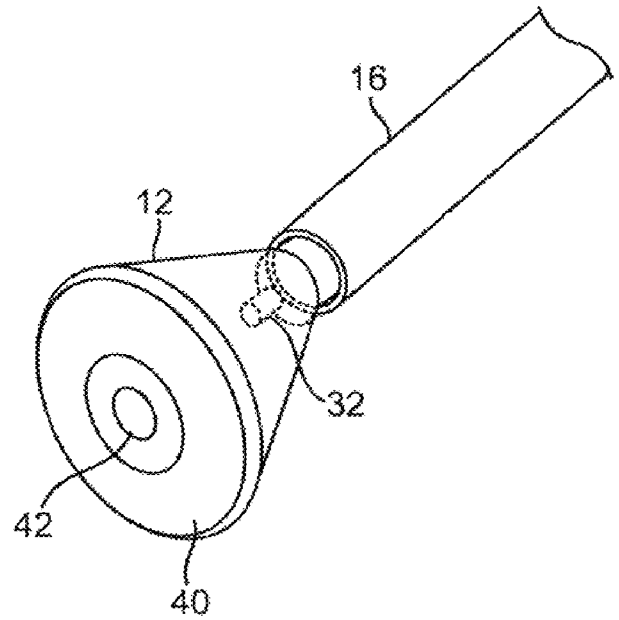
FIGS. 4A and 4B show perspective and end views, respectively, of an imaging hood having at least one layer of a transparent elastomeric membrane over the distal opening of the hood.
Figure 4B:
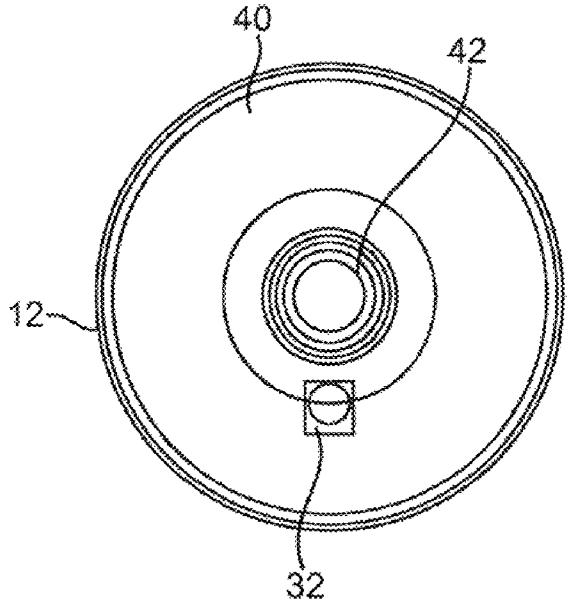

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
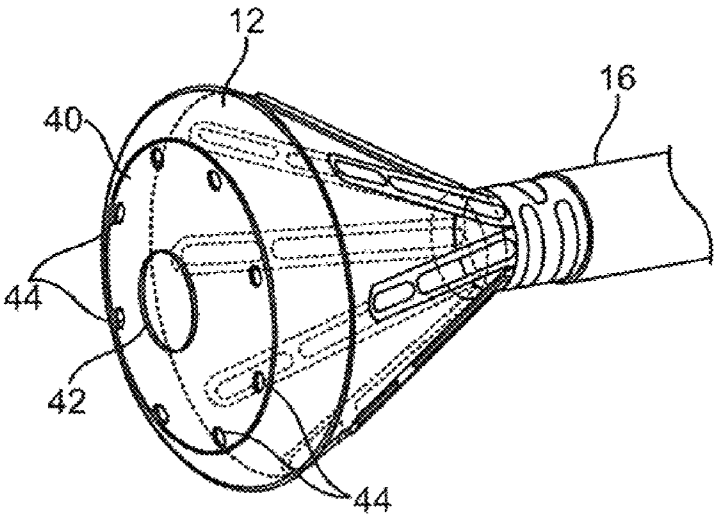
FIGS. 5A and 5B show perspective and end views, respectively, of an imaging hood which includes a membrane with an aperture defined therethrough and a plurality of additional openings defined over the membrane surrounding the aperture.
Figure 5B:
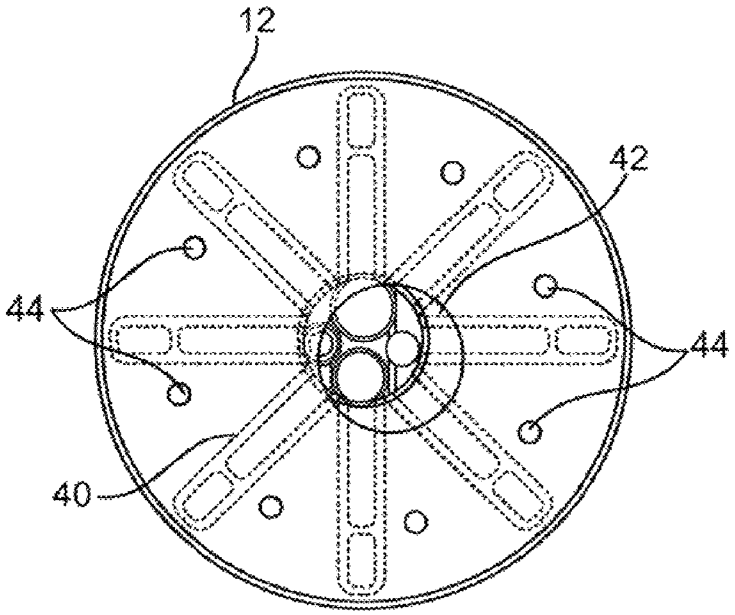

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. patent application Ser. No. 11/259,498 filed Oct. 25, 2005 (U.S. Pat. Pub. 2006/0184048 A1), which is incorporated herein by reference in its entirety.

In utilizing the devices and methods above, various procedures may be accomplished. One example of such a procedure is crossing a tissue region such as in a transseptal procedure where a septal wall is pierced and traversed, e.g., crossing from a right atrial chamber to a left atrial chamber in a heart of a subject. Generally, in piercing and traversing a septal wall, the visualization and treatment devices described herein may be utilized for visualizing the tissue region to be pierced as well as monitoring the piercing and access through the tissue. Details of transseptal visualization catheters and methods for transseptal access which may be utilized with the apparatus and methods described herein are described in U.S. patent application Ser. No. 11/763,399 filed Jun. 14, 2007 (U.S. Pat. Pub. 2007/0293724 A 1), which is incorporated herein by reference in its entirety. Additionally, details of tissue visualization and manipulation catheter which may be utilized with apparatus and methods described herein are described in U.S. patent application Ser. No. 11/259,498 filed Oct. 25, 2005 (U.S. Pat. Pub. 2006/0184048 A1), which is incorporated herein by reference in its entirety.

Figure 6:
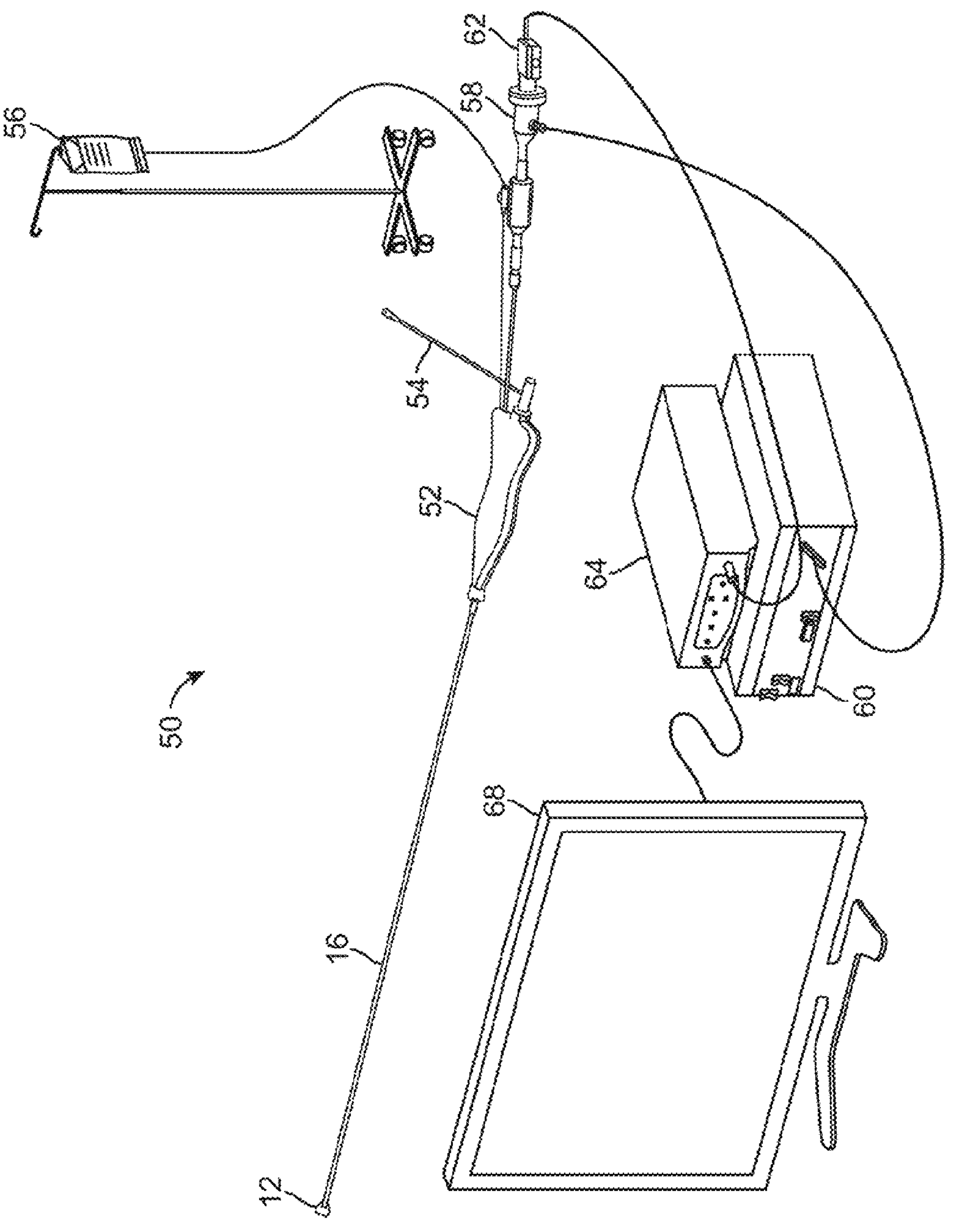
FIG. 6 illustrates an assembly view of another example of a visualization system configured for a controlled articulation and manipulation of the end effector.

FIG. 6 illustrates one example of a system configured to enable direct visualization of tissue underlying hood 12 and optionally tissue treatment, e.g., ablation. As shown in ablation assembly 50, hood 12 and deployment catheter 16 are coupled to handle 52, as previously described. Fluid reservoir 56, shown in this example as a saline-filled bag reservoir, may be attached through handle 52 to provide the clearing fluid and/or ablation medium. An optional access cannula 54 is also illustrated attached to handle 52 and may be used in one variation as an access lumen for flushing or clearing a working channel through handle 52 and catheter 16 where such a working channel may be used to introduce and advance any number of instruments for tissue treatment, e.g., an access needle which may be advanced into handle 52 and into or through hood 12. An optical imaging assembly 58 coupled to an imaging element positioned within or adjacent to hood 12 may extend proximally through handle 52 and be coupled to imaging processor assembly 60 (which may also optionally include a light source) for processing the images detected within hood 12. Assembly may also be coupled to a video receiving assembly 62 for receiving images from the optical imaging assembly 58. The video receiving assembly 62 may in turn be coupled to video processor assembly 64 which may process the detected images within hood 12 for display upon video display 68.

Figure 7A:
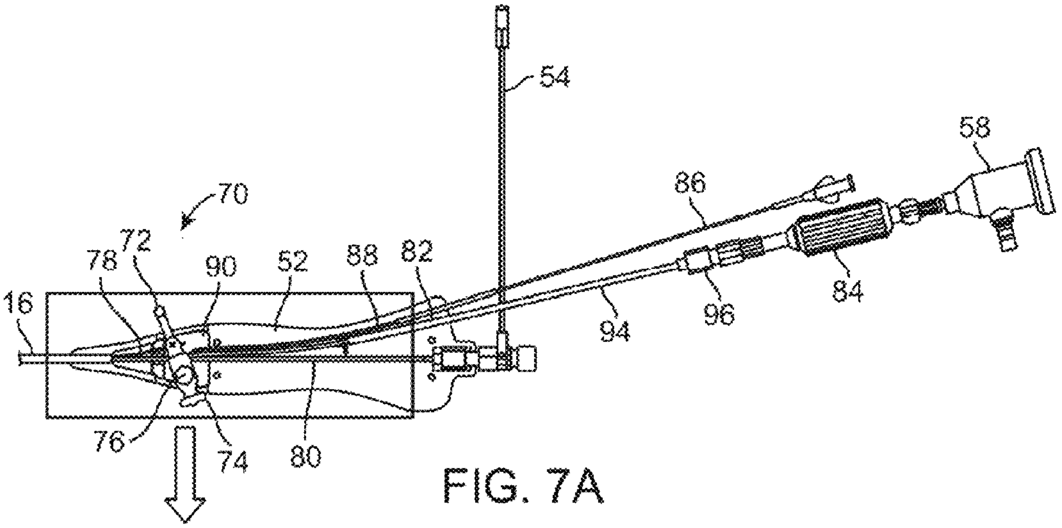
FIG. 7A shows a side view of one example of a handle with access lumens and visualization instrumentation extending therefrom.
Figure 7B:
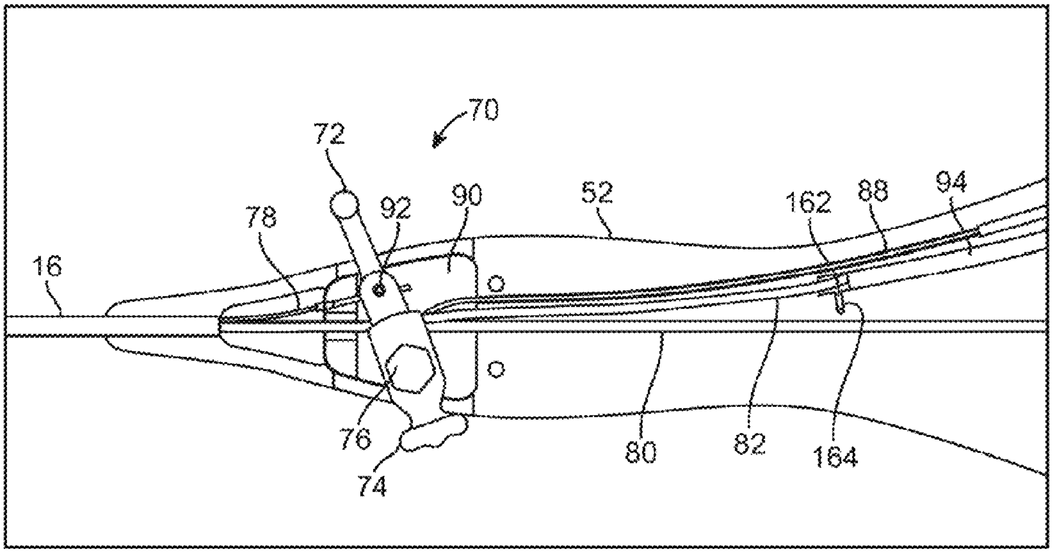
FIG. 7B shows a detail side view of an example of a steering and locking mechanism located upon the handle.

FIGS. 7A and 7B show a side view of a variation of the catheter control handle assembly and a detail side view of the handle 52 having a catheter steering and locking assembly 70 integrated along the handle 52. As shown, handle 52 may have several access channels defined through which allow for communication for any number of instruments into and/or through the catheter 16 and hood 12. For instance, a fluid catheter 86 may be positioned at least partially through fluid channel 88 within handle 52. The optical imaging assembly 58, e.g., a fiberscope or CCD or CMOS imaging assembly, maybe positioned through support shaft 94 and support shaft interface 96 which enters handle 52. In the case where a fiberscope is utilized, the fiberscope shaft 82 may be passed through an optional optical adjustment assembly 84, as described in further detail below. Another working channel 80 may be further defined through handle 52 to allow for entry and passage of yet another instrument, e.g., a piercing needle, ablation probe, etc.

Also shown is catheter steering and locking assembly 70 integrated along the handle 52 having a steering member 72 pivotably coupled to a locking member 74. Steering member 72 may be coupled to one or more pullwires 78 attached thereto via retaining member 92, e.g., set screw, such that manipulation of the steering member articulates the steerable section and hood in a corresponding manner. Steering member 72 may be pivotably coupled to locking member 74 along a point of rotation and locking mechanism 76 which is attached to a steering plate 90.

The catheter shaft contains at least one lumen which allows the passage of one or more pullwires that are connected to the steering member 72 at the proximal end of the pullwire while the distal end may be terminated and anchored to the steering mechanisms along the steerable portion 100 of the catheter 16. Details of steering mechanisms and steerable sections of the visualization catheter, which may be utilized with apparatus and methods described herein are described in U.S. patent application Ser. No. 12/108,812 filed Apr. 24, 2008 and Ser. No. 12/117,655 filed May 8, 2008, each of which is incorporated herein by reference in its entirety. The one or more pullwires can be made from metal such as stainless steel or nitinol. A compression coil, e.g., made of stainless steel, with a slightly larger diameter than the pullwire may be positioned about the pullwire within the handle 52 to allow the pullwire to slide freely therethrough. The ends of the compression coil may be glue jointed to the proximal end to the catheter body and the distal end to the side wall of the shaft. Alternatively, the pullwire may be passed through a hypo tube made of stainless steel and be anchored at the distal side wall of the catheter 16.

Figure 8A:
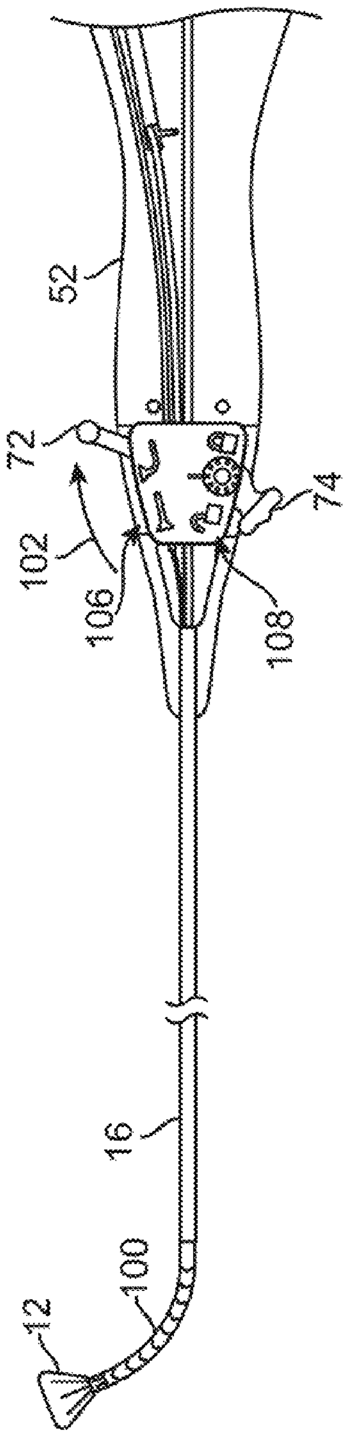
FIGS. 8A and 8B show side views of an example of a visualization and treatment catheter having a steerable distal end articulated by a steering member and locked into position.
Figure 8B:
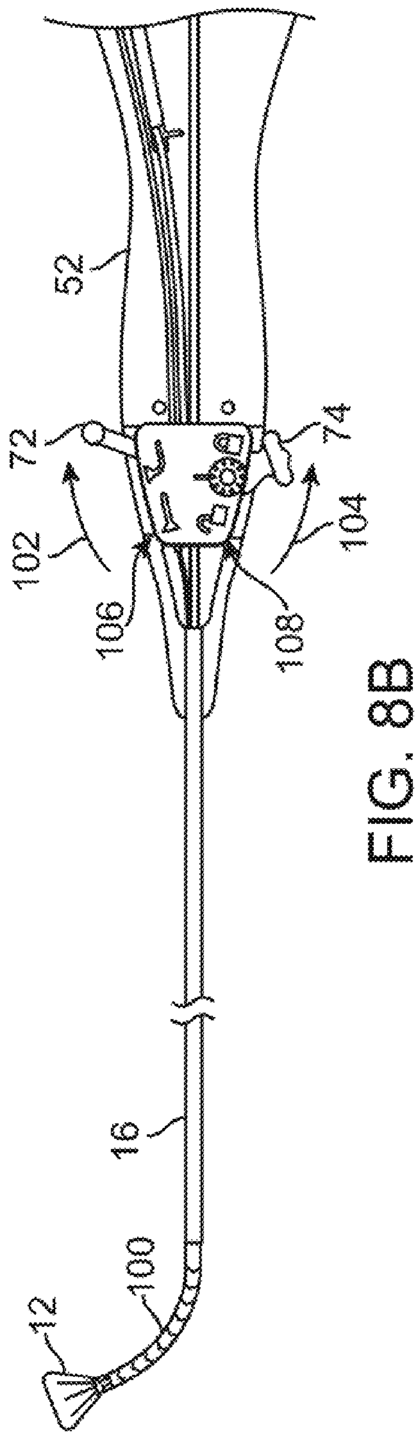

In use, steering member 72 may be actuated, e.g., by pulling the member proximally, to articulate the steerable portion 100 and hood 12 in the same direction of articulation 102, as shown in the side view of FIG. 8A. With the steerable portion 100 articulated to the degree desired to position hood 12, locking member 74 may be actuated, e.g., in the direction of locking 104, to maintain a configuration of steerable portion 100 and hood 12 by preventing or inhibiting movement of steering member 72, as shown in the side view of FIG. 8B, thus freeing the hand or hands of the user. A steering indicator 106 and/or locking indicator 108 may be optionally incorporated along handle 52 as a reminder to the user.

Figure 9:
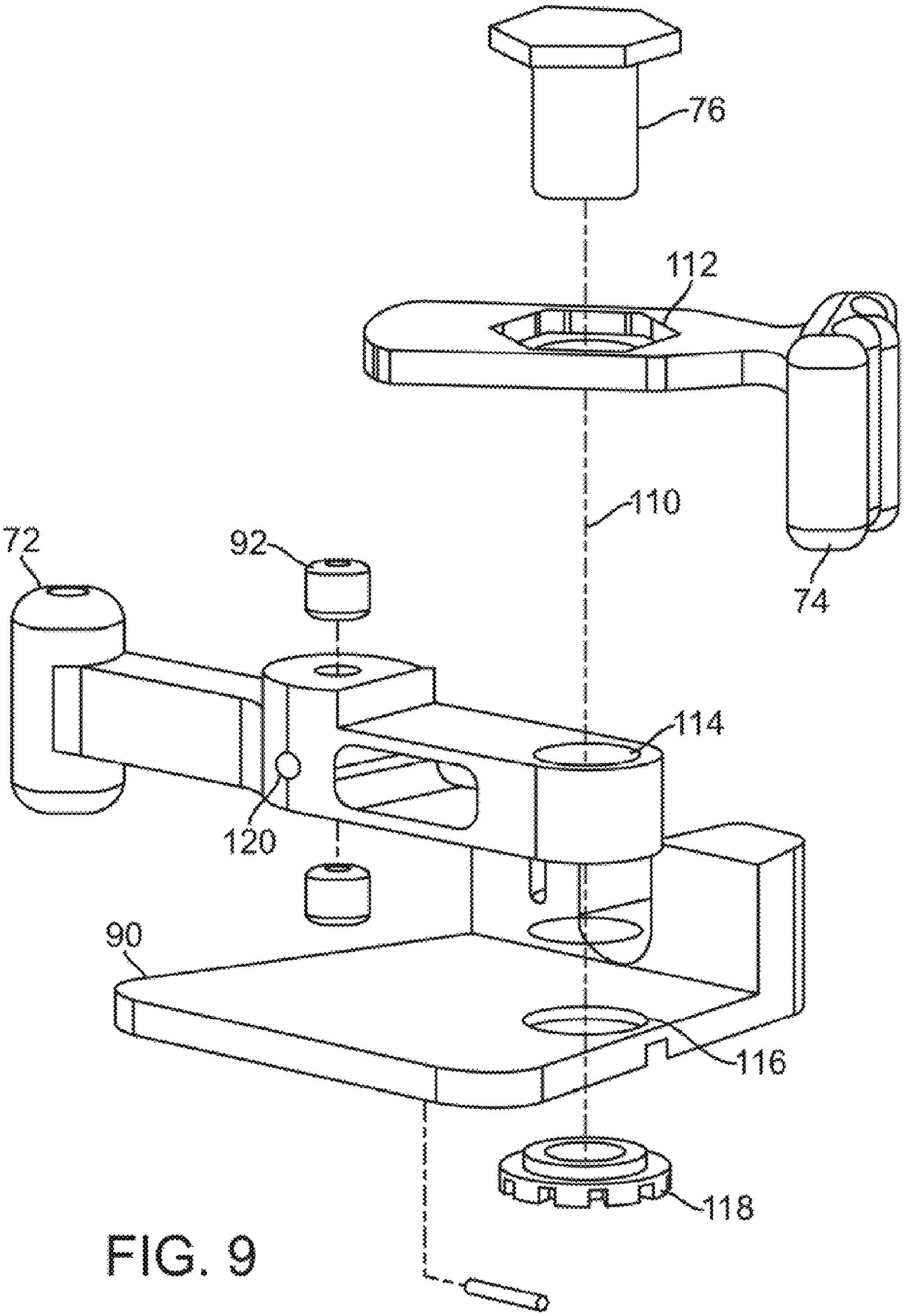
FIG. 9 shows a perspective exploded assembly view of an example of the catheter steering and locking assembly.

FIG. 9 illustrates a perspective view of an exploded steering and locking assembly. As shown, the locking member 74 may define an opening 112 which is keyed to locking mechanism 76, e.g., lock hex nut, such that the locking mechanism 76 rotates when locking member 74 is rotated. Locking mechanism 76 may also pass through an opening 114 defined along the steering member 72 as well as through an opening 116 defined through the steering plate 90 such that a terminal end of the locking mechanism 76 is coupled to lock bolt 118. Once the one or more pullwires, which may be secured within pullwire passage 120 defined through the steering member 72 by set screw 92, is pulled to a desired degree by steering member 72, locking member 74 may be rotated about axis of rotation 110 to drive locking mechanism 76 into the lock bolt 118 to compress the steering member 72 between the steering plate 90 and the locking member 74. Hence, steering member 72 is locked in its current position when locking member 74 is applied thereby holding the steerable section in its desired configuration.

Figure 10A:
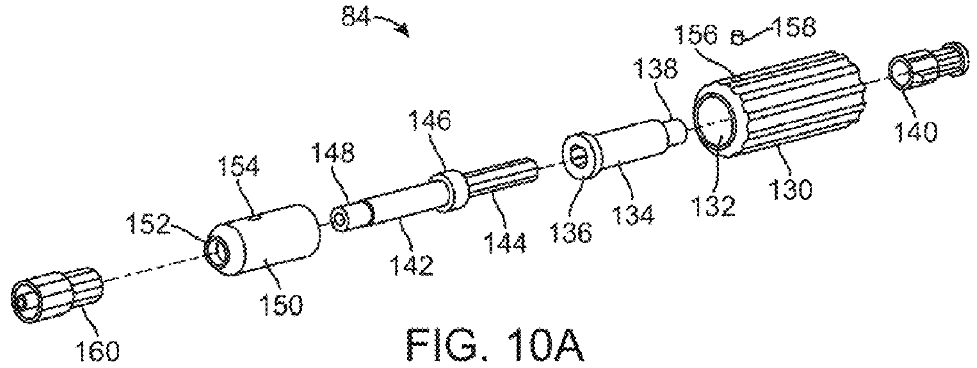
FIG. 10A shows a perspective exploded assembly view of an optional optical adjustment assembly which may be used to provide for zooming in and out of a visualization instrument, such as a fiberscope, through the catheter.
Figure 10B:
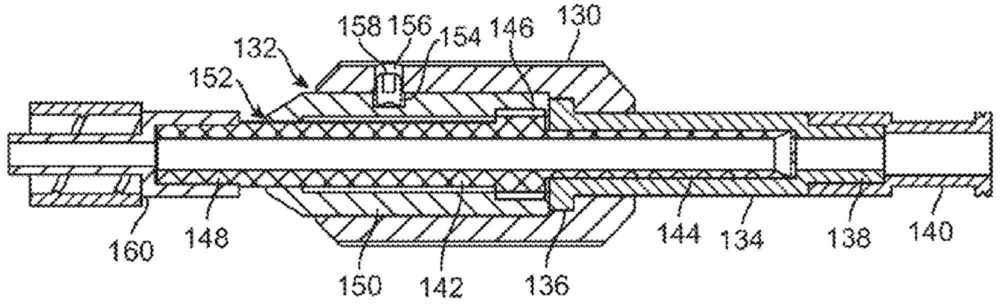
FIGS. 10B and 10C illustrate cross-sectional side views of the optical adjustment assembly showing the relative movement of the assembly to convey the visualization instrument distally and proximally to adjust visual images.
Figure 10C:
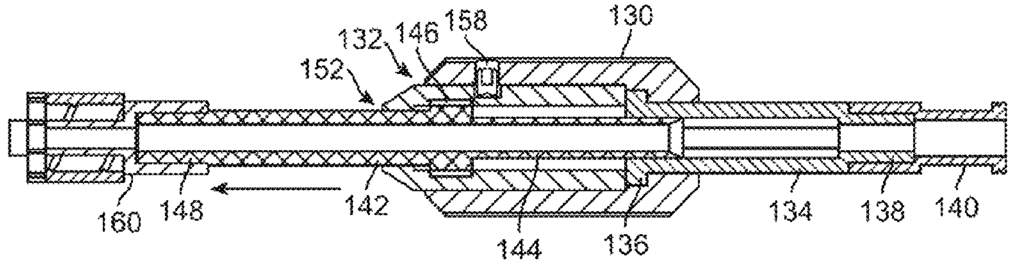

As previously mentioned, the handle assembly may also optionally incorporate an optical adjustment assembly 84, as shown in the perspective exploded assembly view of FIG. 10A. The optical adjustment assembly 84 may be used to move the distal lens of a visualization instrument, such as a fiberscope, distally or proximally from the imaged tissue region, hence simulating a zoom-in and/or zoom-out optical effect. Generally, the optical adjustment assembly 84 is able to provide zoom-in and/or zoom-out capabilities by varying the length of the assembly. As depicted in the cross-sectional side views of FIGS. 10B and 10C, an adjustment member 130 houses guide shaft 134 which extends proximally through receiving channel 132 of adjustment member 130 and is retained within by a retaining lip 136. The proximally extending sliding shaft portion 144 of a second shaft is positioned slidably within guide shaft 134 while the distally extending distal shaft portion 142 of this second shaft is positioned within a sleeve opening 152 of retaining sleeve 150, which is also positioned within adjustment member 130. This second shaft further comprises a threaded guide 146 along a portion of its outer surface which is configured to engage rotatably with the inner surface of sleeve opening 152, which is also threaded in a complementary manner.

With the shafts assembled, one or more fasteners 158, e.g., set screw, may be used to secure adjustment member 130 to retaining sleeve 150 through fastener opening 156 defined through member 130 and fastener interface 154 defined along retaining sleeve 150. Distally extending distal shaft portion 142 may further define connector interface 148 for coupling to a retaining luer connector 160 while guide shaft 134 may also define a connector interface 138 for coupling to a luer connector 140. In use, the shaft of a visualization instrument such as a fiberscope may be positioned through and secured to the assembly 84 by one or more of the connectors, e.g., luer connector 160. By rotating adjustment member 130, which is coupled to retaining sleeve 150, distal shaft portion 142 may be advanced or retracted relative to guide shaft 134 via the threaded engagement between threaded guide 146 and sleeve opening 152. The assembly 84 may be accordingly varied in length while distally or proximally advancing the fiberscope based on the varied length of the optical adjustment assembly 84 to control the visualized field of view.

Figure 11:
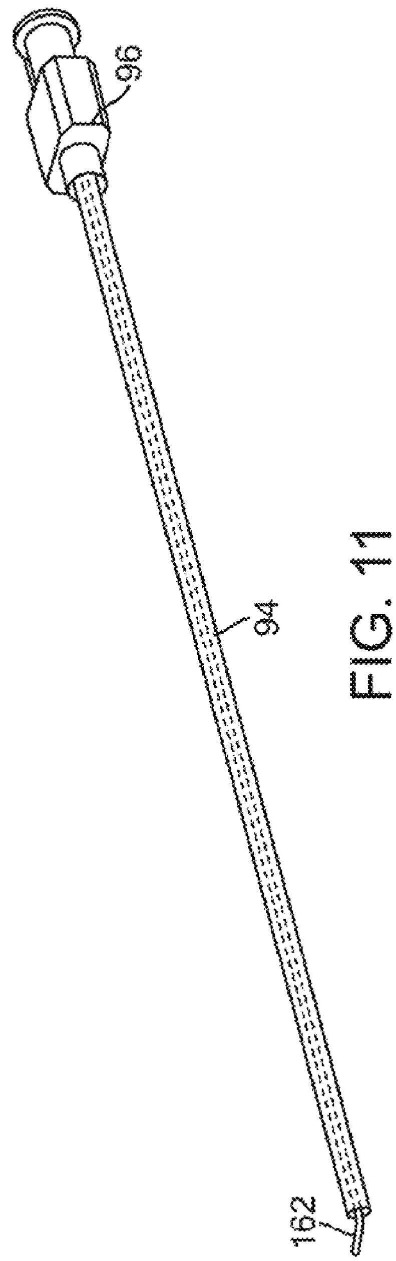
FIG. 11 shows a perspective view of an optional access cannula having a stabilizing strain-relief wire for coupling to a handle.

Also previously mentioned above, the optical imaging assembly 58 may be optionally positioned through a support shaft 94 and support shaft interface 96 which enters handle 52, as shown in the perspective view of FIG. 11. Support shaft 94 may be longitudinally reinforced to protect the optical fiber used by the visualization catheter from buckling or breaking. To maintain a position of shaft 94 relative to the handle into which the shaft 94 extends, shaft 94 may incorporate a strain relief wire 162 which protrudes from the distal end of shaft 94 at an angle for temporarily locking within a wire channel 164, as shown above in FIG. 7B. Once wire 162 has been engaged within channel 164 within the handle, shaft 94 may provide stability to the fiberscope shaft. The wire 162 can be made from stainless steel or nitinol and have a thickness between, e.g., 0.050" to 0.100".

Figure 12:
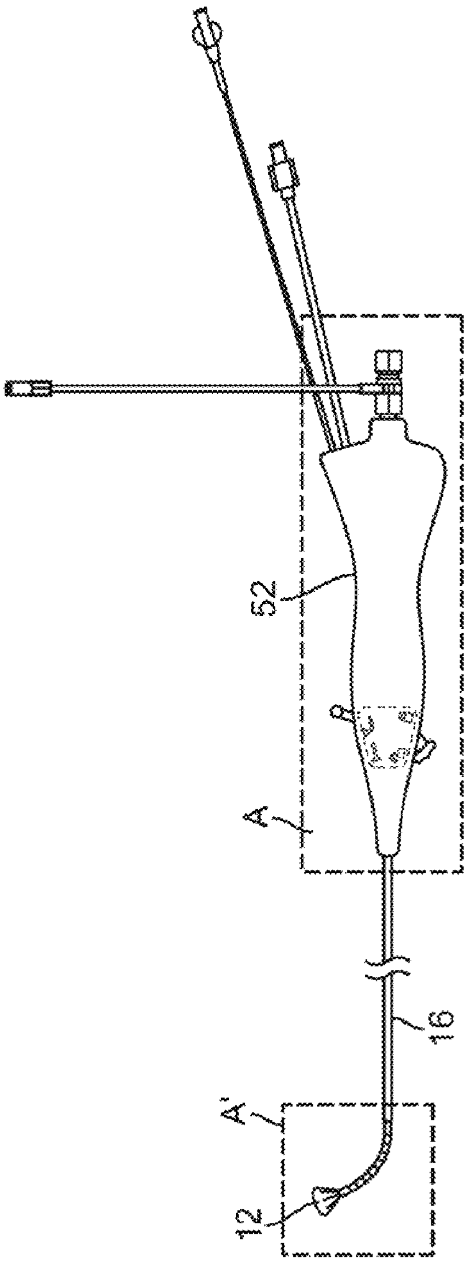
FIG. 12 shows a side view of a handle assembly positioned to lie within a first plane correspondingly aligned with a second plane defined by a deflection of the steerable distal section.

Because manipulation of the hood 12 and steerable portion corresponds with an angle at which the handle is positioned, handle 52 may also serve as an orientation indicator for the hood 12 and steerable portion once the hood 12 has been introduced into the patient's body. As shown in the side view of FIG. 12, the handle 52 may define a plane A. Articulation of hood 12 and the steerable portion may thus also define a plane A' which corresponds planarly to the plane A defined by the handle 52. This correspondence between the planes A, A' of the handle 52 and the resulting articulation of the hood 12 and steerable portion may be particularly useful for efficiently controlling the hood position within the patient's body. As the catheter 16 is usually repeatedly torqued during a procedure, keeping track of the orientation of the deflection of the hood 12 can be difficult, if not impossible, unless fluoroscopy is used. With the handle 52, the angle of deflection of the hood 12 can be predicted by the operator without the need of fluoroscopy. This is can be particularly desirable in procedures such as transseptal punctures where an accurate angle of puncture of the septal wall is desirable to avoid complications such as perforation of the aorta.

Figure 13A:
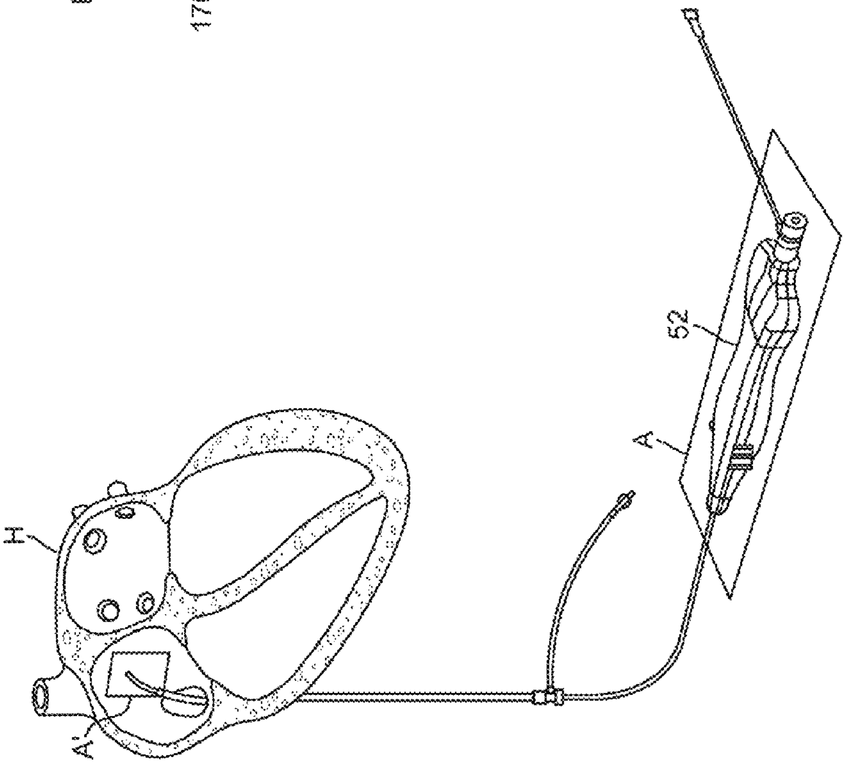
FIGS. 13A and 13B show an example where a visualization hood has been advanced intravascularly within a patient's heart with a handle positioned external to the patient and illustrates how re-orienting the handle, e.g., by 90°, results in a corresponding articulation of the plane defined by the visualization hood and distal section within the heart.
Figure 13B:
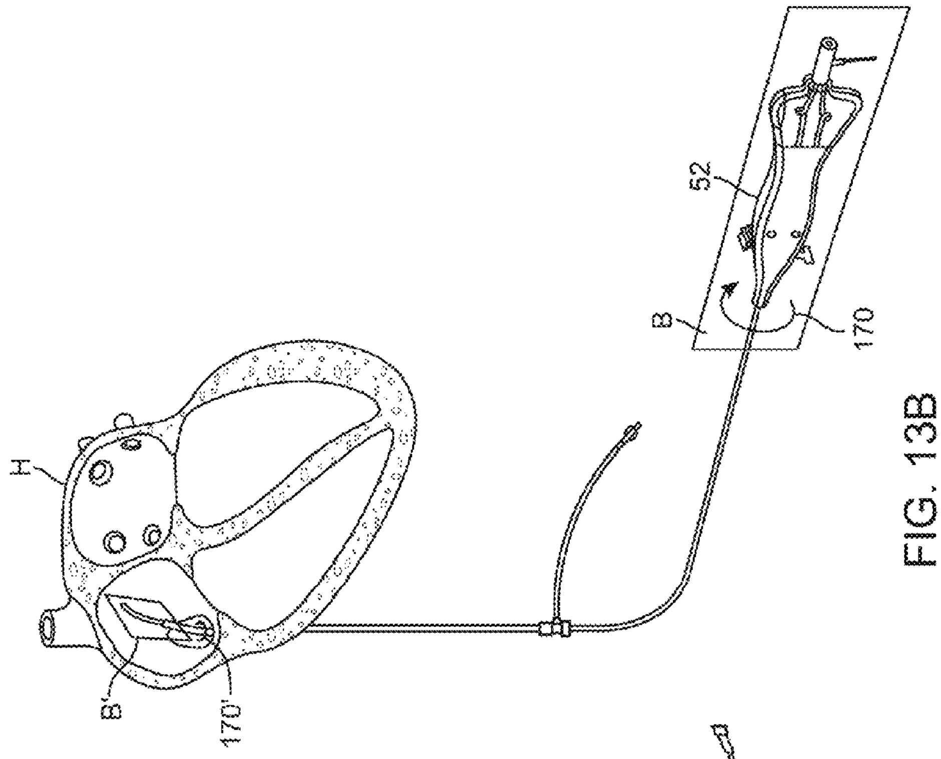

An example of how this feature may be utilized is shown in the illustrations of FIGS. 13A and 13B, which show a hood positioned within the right atrium of a heart H while coupled to handle 52 positioned external to the body. Handle 52 may be seen as being positioned along plane A while hood 12 and the distal portion of catheter 16 is positioned within corresponding plane A'. As handle 52 is rotated, e.g., at 90°, about its longitudinal axis in a direction of rotation 170 such that handle 52 then lies within a different plane B, hood 12 and the distal steerable portion may also rotate, e.g., at 90°, within the right atrium in a corresponding direction of rotation 170' such that the hood and catheter then define a corresponding different plane B'. Thus, by merely articulating the handle 52 external to the body in a specified direction, the user may adjust or desirably position or re-position the hood within the body in a known direction without having to utilize additional catheter positioning mechanisms.

Figure 14:
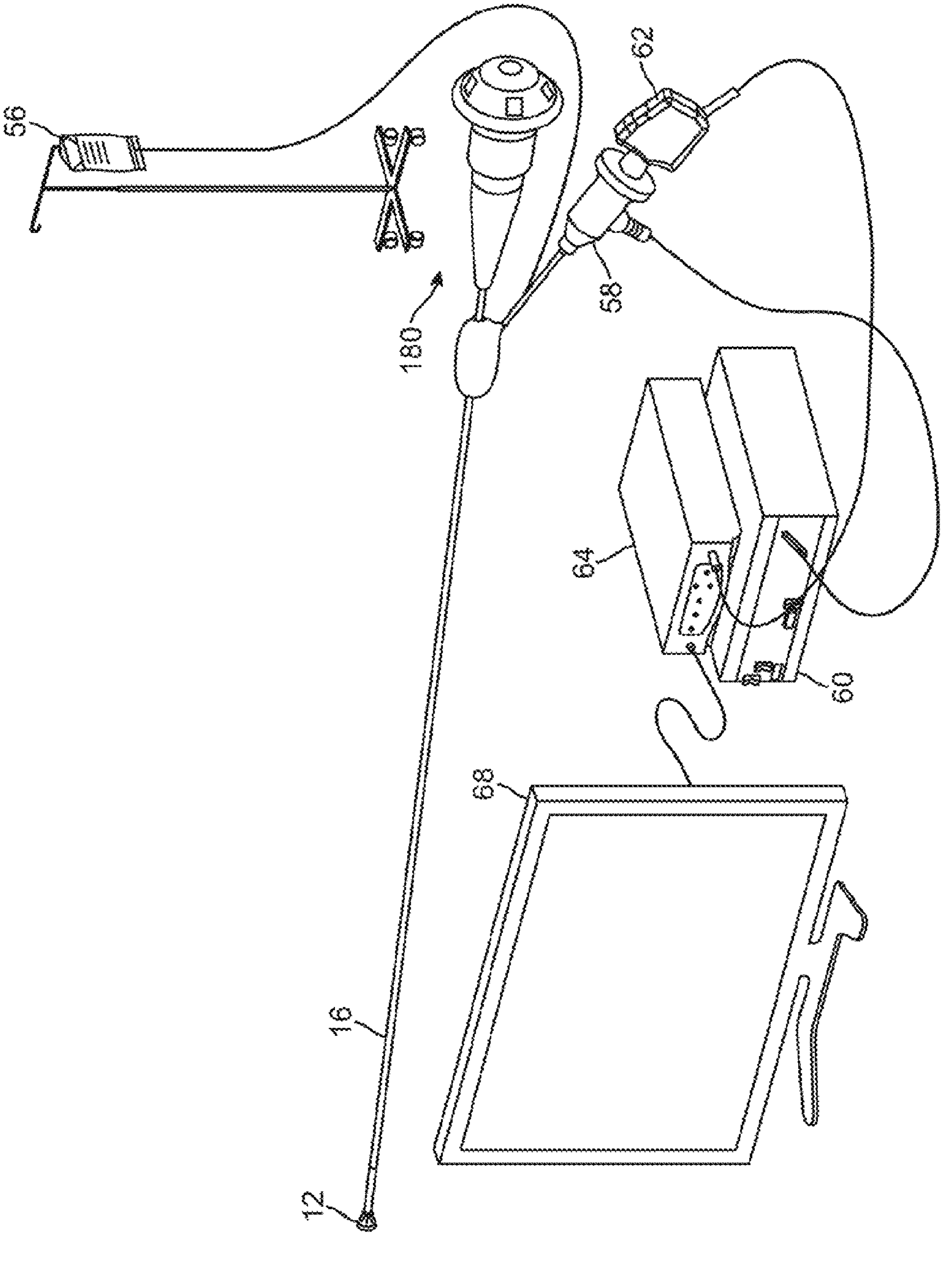
FIG. 14 shows an assembly view of another variation of the handle which is configured to manipulate the steerable distal section in multiple directions by a single hand of the user.
Figure 15:
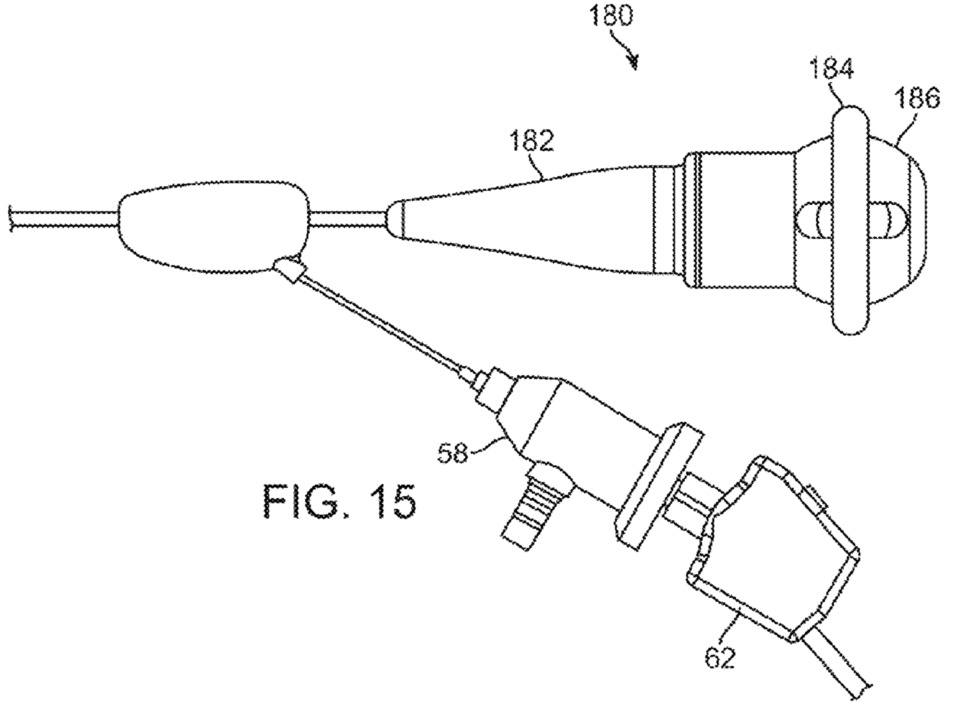
FIG. 15 shows a detail side view of the handle of FIG. 14.
Figure 16:
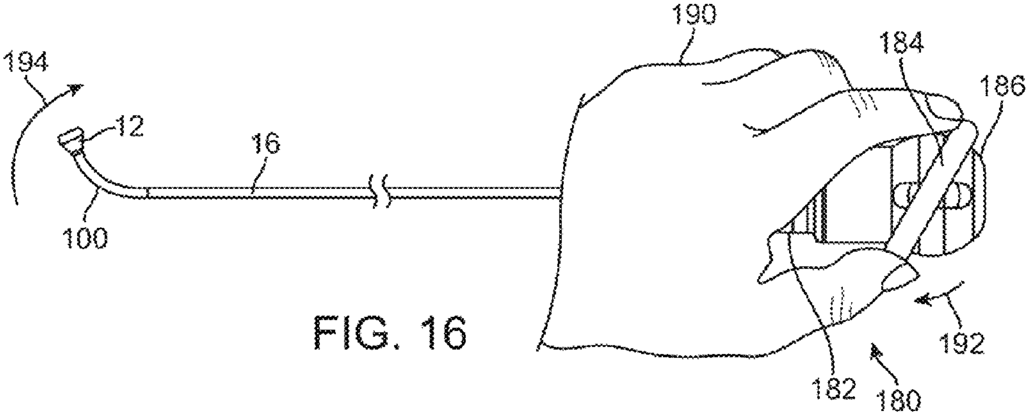
FIG. 16 illustrates a single hand of the user manipulating a multi-directional steering ring located on the handle.

FIG. 14 shows an assembly view of another variation of a steering handle assembly 180 which enables a user to steer the visualization hood 12 along at least four or more degrees of freedom relative to a longitudinal axis of the catheter 16. FIG. 15 shows a side view of the handle assembly 180 illustrating handle portion 182 and steering ring 184 which may be manipulated along any number of directions relative to housing 186 to control the articulation of the hood 12. As shown in FIG. 16, manipulating or pulling along a portion of steering ring 184, e.g., along a direction of actuation 192, causes steerable portion 100 and hood 12 to move along a corresponding direction of articulation 194. Moreover, because of the manner in which steering ring 184 is positioned to encircle the handle assembly 180, the operator may grip the handle 180 along any orientation and operate the handle assembly 180 with a single hand 190. For instance, the operator may manipulate the steering ring with the thumb and/or index finger while insertion length of the catheter 16 can also be simultaneously controlled by the same hand 190 by pulling or pushing the handle assembly 180 to translate the entire catheter 16.

Figure 17A:
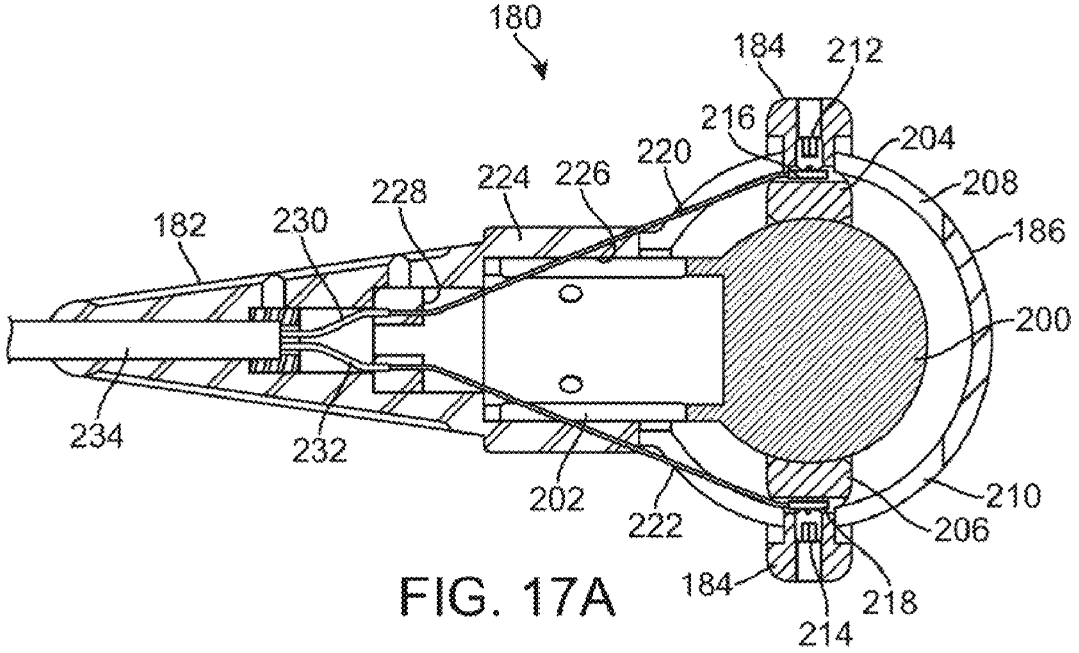
FIGS. 17A and 17B show cross-sectional side views of the handle illustrating the multiple pullwires attached to the steering ring.
Figure 17B:
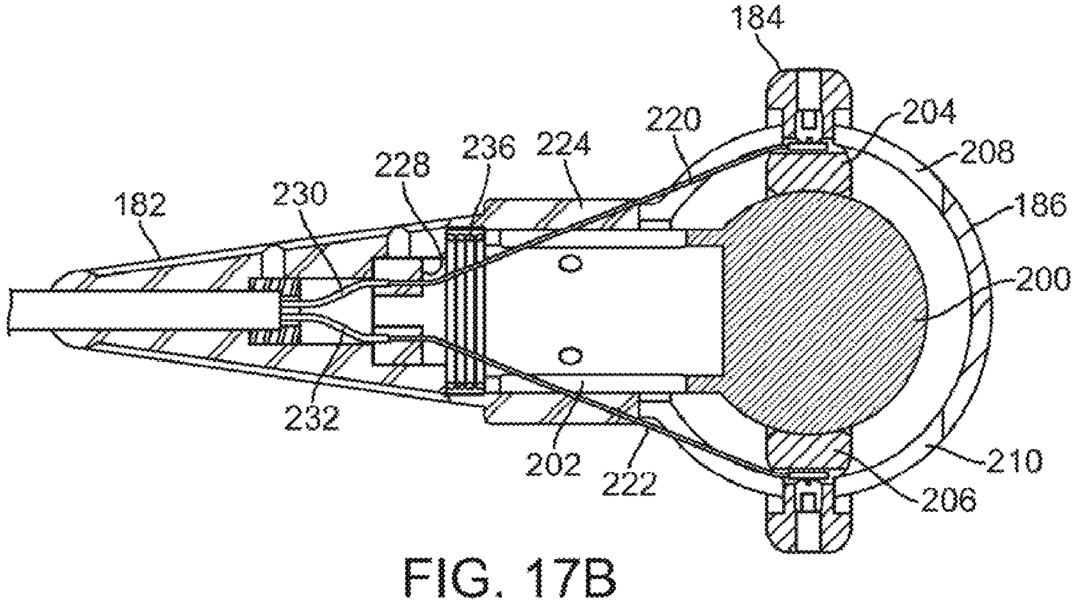

As shown in the cross-sectional side views of FIGS. 17A and 17B, handle assembly 180 may generally comprise a ball pivot 200 supported by pivot support 202 enclosed within housing 186. Ball pivot 200 may support the steering ring 184 via one or more steering ring support members 204, 206, e.g., four steering ring support members, which extend radially through corresponding support member openings 208, 210. Because of the ball pivot 200 shape, steering ring 184 may be moved about pivot 200 in any number of directions. The terminal ends of one or more pullwires 220, 222 may be coupled steering ring 184 via corresponding fasteners 212, 214, e.g., set screws, securing each of the pullwire termination crimps 216, 218. These pullwires 220, 222 may extend through pivot support housing 224 which defines receiving channel 226, which supports pivot support 202, and through pullwire transition manifold 228 and into a proximal end of a multi-lumen shaft 234, such as catheter 16. The pullwires may continue distally through catheter 16 where they are coupled to the steerable portion of catheter 16. Each of the pullwires may be optionally encased in corresponding compression coils 230, 232 between the transition manifold 228 and catheter.

Although multiple pullwires may be utilized depending upon the number of directions for articulation, four pullwires may be typically utilized. Each of the four pullwires may be terminated symmetrically around a circumference of steering ring 184 such that a balanced four-way steering of the distal portion may be accomplished, although manipulating the steering ring 184 along various portions of its circumference may yield combinational articulation between the pullwires to result in numerous catheter configurations. Additionally, the handle assembly may further incorporate a spring mechanism 236 as an overdrive prevention mechanism, as shown in FIG. 17B. Spring mechanism 236 may be positioned between the transition manifold 228 and ball pivot 200 in order to prevent over-tensioning or breaking of the pullwires if the steering ring 184 is over-deflected in a direction.

Figure 18A:
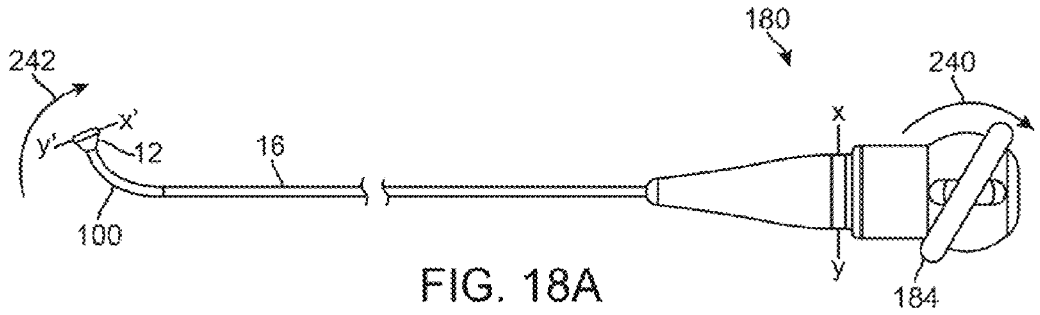
FIGS. 18A to 18C show side views of the handle assembly illustrating how the handle is configured to articulate and steer the visualization hood consistently in the same direction when urged by the steering ring in the same direction regardless of the handle orientation.
Figure 18B:
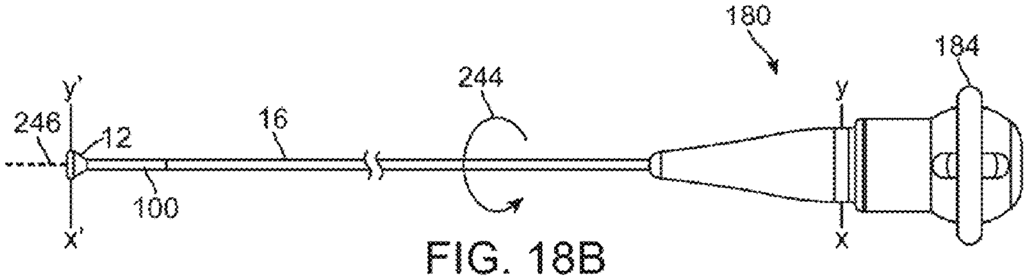
Figure 18C:
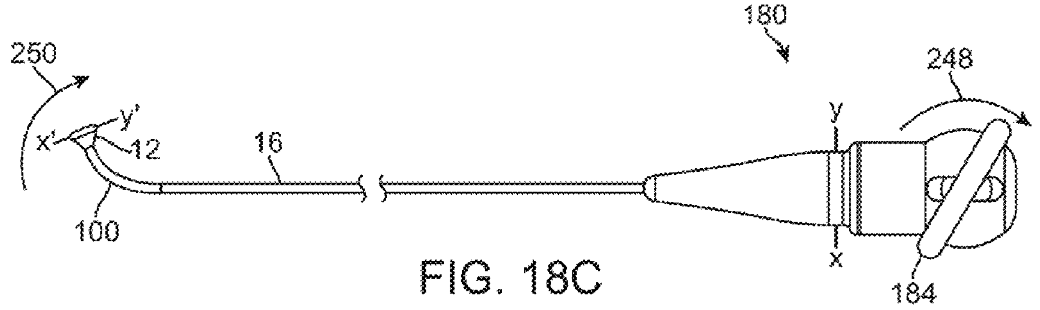

FIGS. 18A to 18C illustrate side views of the handle assembly 180 and catheter 16 to show how the hood 12 can be consistently deflected in the same direction by which the steering ring 184 is being deflected regardless of the orientation of the handle assembly 180. For example, handle assembly 180 may be deflected in a direction of actuation 240 such that hood 12 is deflected in a corresponding direction of articulation 242. A first side indicator X of handle 180 and a second opposing side indicator Y of handle 180 are shown to indicate a first position of handle 180 and the corresponding first side indicator X' of hood 12 and corresponding second opposing side indicator Y' of hood 12 are likewise shown to indicate a first position of hood 12. The handle assembly 180, catheter 16, and hood 12 are then rotated along an arbitrary direction of rotation 244 about longitudinal axis 246 of the assembly such that the handle positional indicators X, Y and the hood positional indicators X', Y' are now positioned in opposite locations. Even with the entire assembly rotated, e.g., 180°, actuating the steering ring 184 along the direction of actuation 248 still results in a corresponding direction of articulation 250 of hood 12 which matches the initial direction of articulation 242 despite the rotated assembly. Regardless of the angle by which the operator subsequently rotates the catheter 16 about the longitudinal axis 246, the operator can still be certain that deflecting the steering ring 184 in a particular direction will steer the distal end of the catheter in the same direction. This removes the need for the operator to memorize the original position of the catheter or how much the catheter has been torqued in order to gauge the orientation of the deflected end when the catheter is inserted into the patient.

Figure 19:
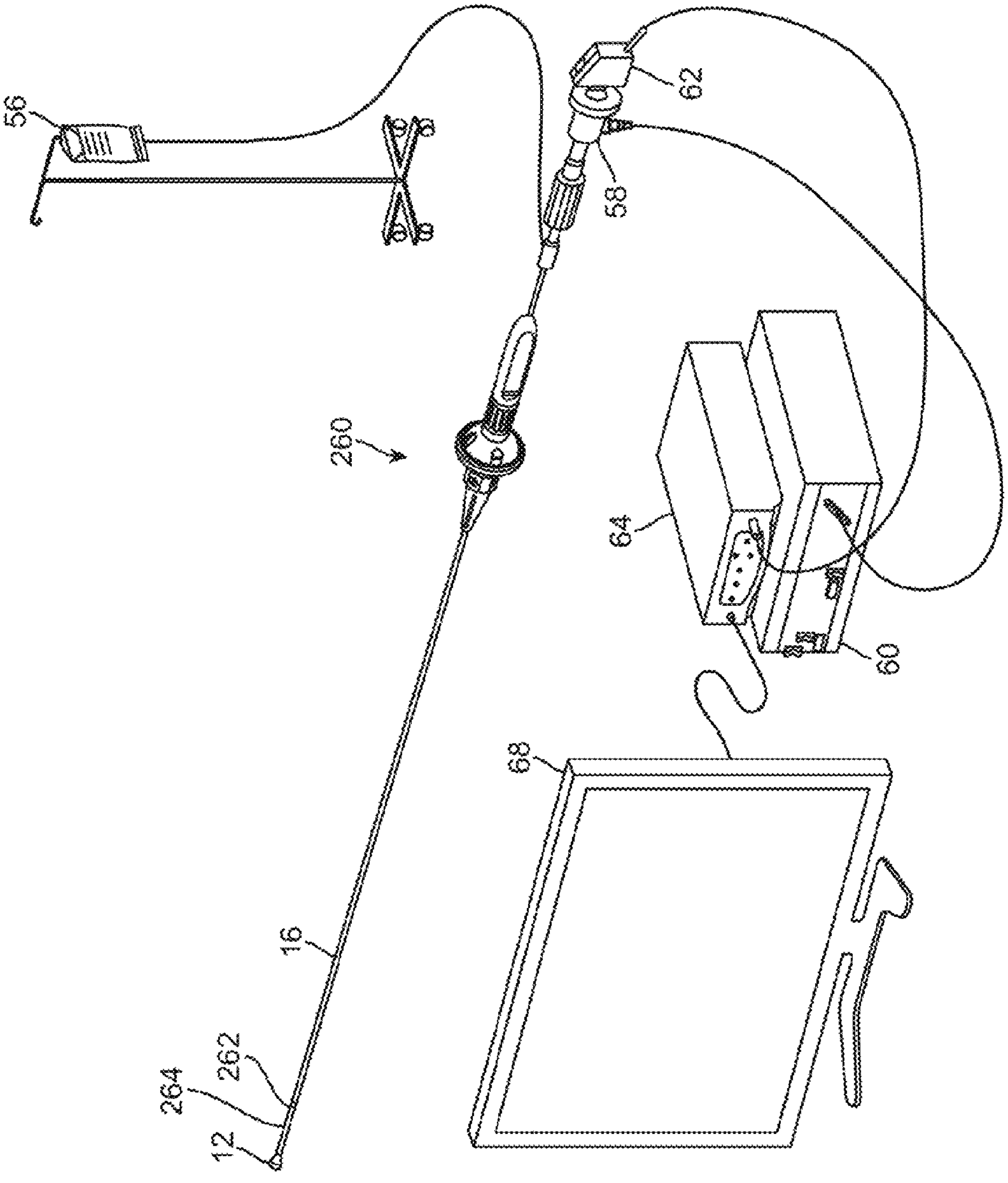
FIG. 19 shows an assembly view of yet another variation of the handle which is configured to manipulate the steerable distal section in multiple directions as well as curve yet another steerable section located proximal to the distal section.

In yet another variation of the catheter control handle, FIG. 19 shows an assembly view of steering handle assembly 260 which is configured to articulate a catheter 16 having at least two independently deflectable portions, e.g., a proximal steerable section 262 adapted to articulate within a single plane relative to a longitudinal axis of the catheter and a distal steerable section 264 adapted to articulate within one or more planes relative to a longitudinal axis of the proximal steerable section 262. Utilizing such catheter steering may be particularly advantageous for tissue treatment, e.g., ablation, in the left atrium of the heart as such adaptability in steering may impart additional accuracy and efficiency to steer the imaging and ablation hood 12 around complex anatomical structures, such as the pulmonary vein ostium. Examples of such steerable catheters are shown and described in further detail in U.S. patent application Ser. No. 12/108,812 filed Apr. 24, 2008 (U.S. Pat. Pub. 2008/0275300 A1) and Ser. No. 12/117,655 filed May 8, 2008 (U.S. Pat. Pub. 2008/0281293 A1), each of which is incorporated herein by reference in its entirety.

Moreover, this handle variation as well as any of the other handle variations herein may incorporate any of the features described in each of the variations, as practicable. For instance, this particular variation may also utilize the optical adjustment assembly, locking mechanisms, etc. in combination if so desired.

Figure 20A:
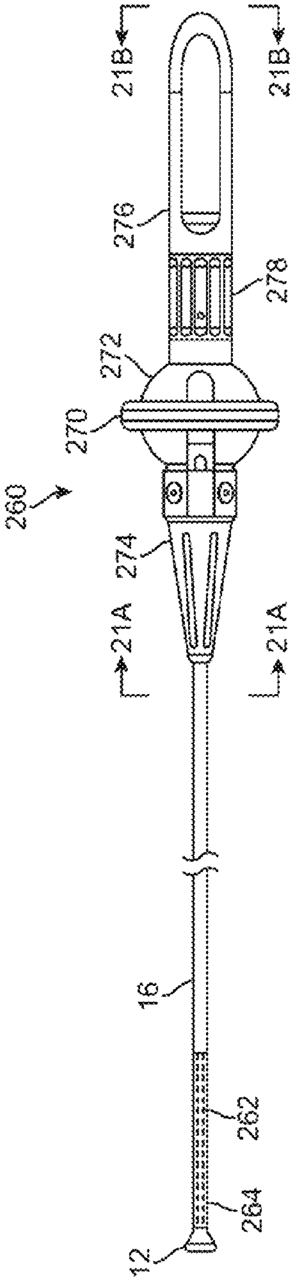
FIGS. 20A and 20B show side views, respectively, of the catheter control system handle.
Figure 20B:
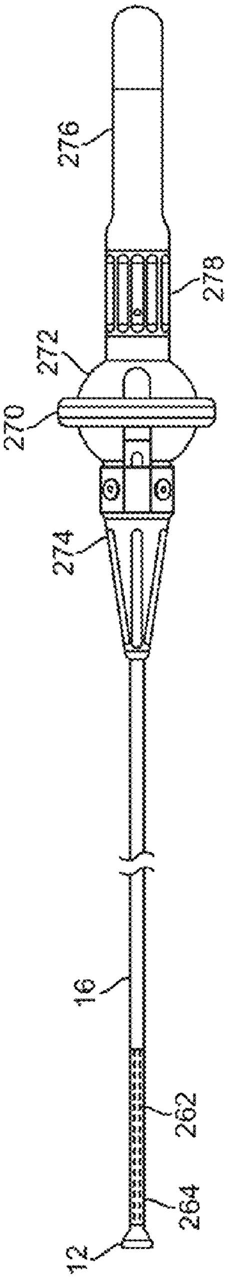
Figure 21A:
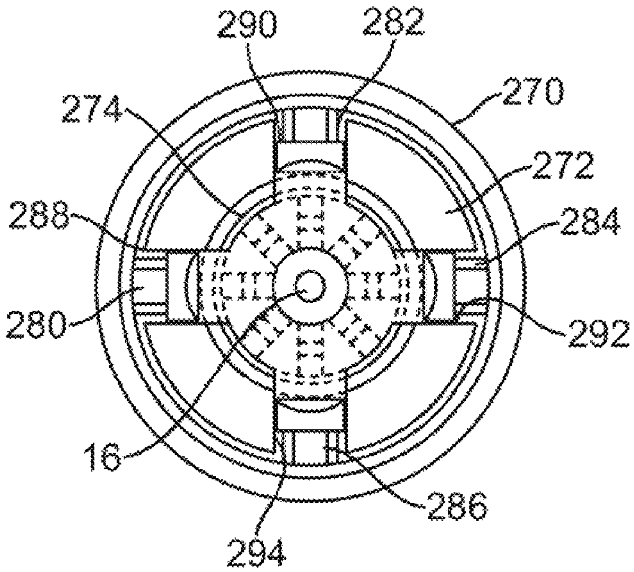
FIGS. 21A and 21B show end views of the catheter control handle from the perspective of the catheter shaft and from the handle end, respectively.
Figure 21B:
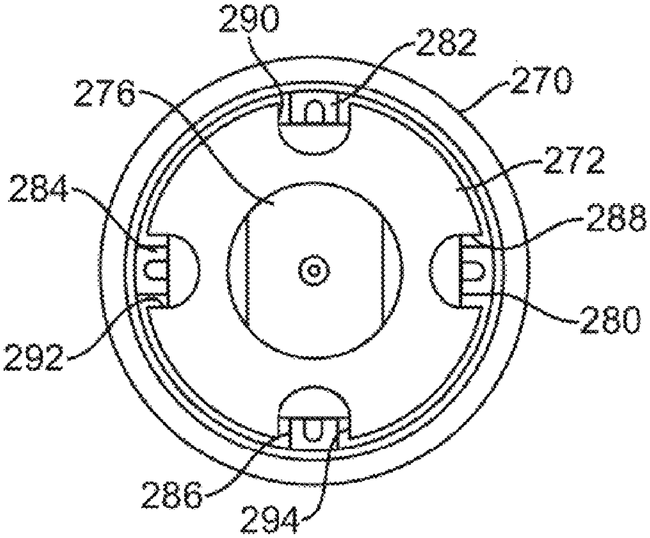
Figure 22A:
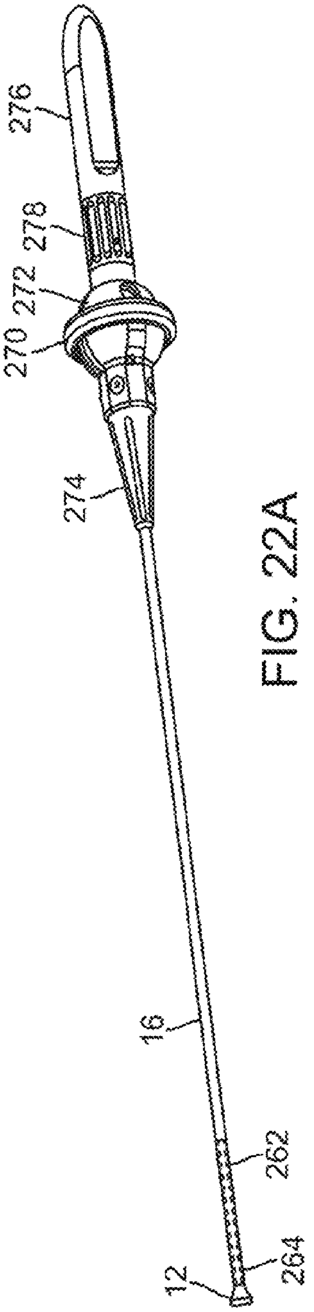
FIGS. 22A and 22B show perspective assembly and detail views, respectively, of the visualization assembly and catheter control handle.
Figure 22B:
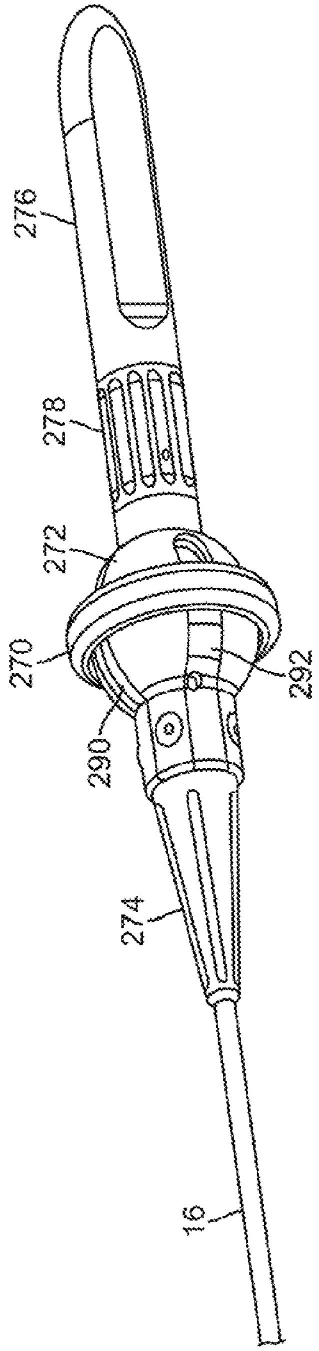

FIGS. 20A and 20B show side views of the steering handle assembly 260 with the catheter 16 having proximal steerable section 262 and distal steerable section 264 extending from distal handle portion 274. As with previous variations, a steering ring 270 may encircle housing 272. However, this variation further includes a proximal handle portion 276 extending from housing 272 with a proximal section control 278 for articulating proximal steerable section 262. FIGS. 21A and 218 show end views of the control handle 260 from the perspective of the catheter shaft 16 and from the handle end, respectively. As shown, steering ring 270 may be supported by a number of steering ring support members 280, 282, 284, 286 which extend from housing 272 through corresponding support member openings 288, 290, 282, 294. FIGS. 22A and 22B show additional perspective assembly and detail views, respectively, of the visualization assembly and steering handle assembly 260.

Figure 23A:
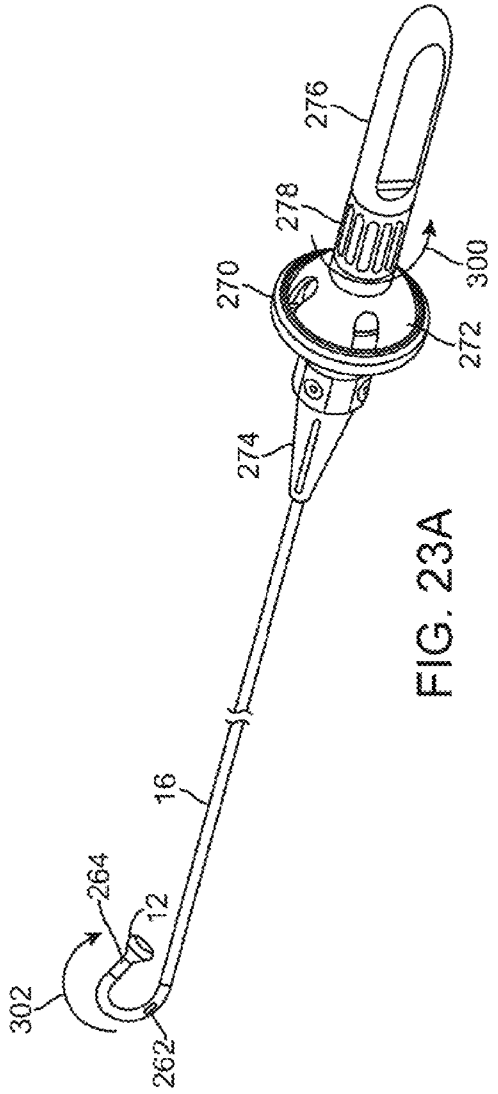
FIG. 23A shows a perspective view of a steerable proximal portion of the catheter actuated by a proximal section control located along the handle.
Figure 23B:
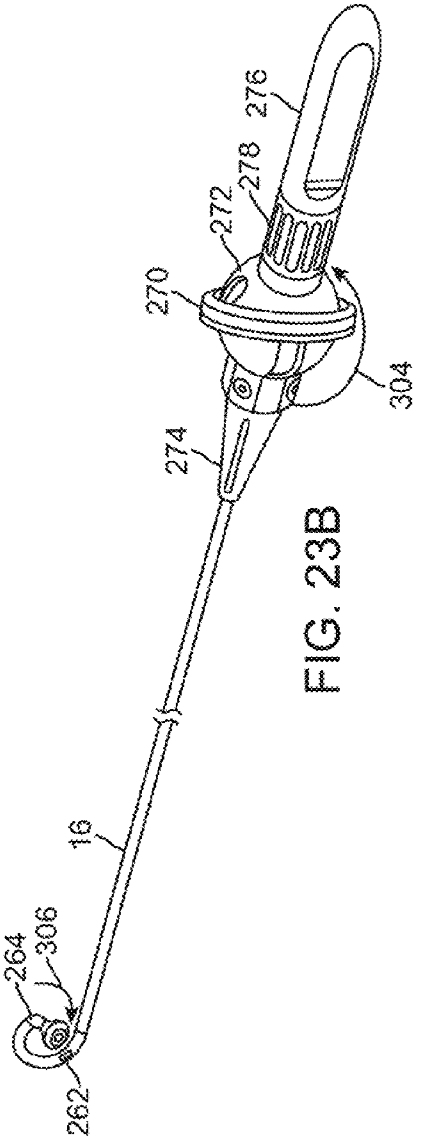
FIG. 23B shows a perspective view of the steerable distal portion of the catheter further steered by actuation of the steering ring to maneuver the visualization hood relative to the steerable proximal portion.

As previously described for other variations, this particular handle assembly 260 may be used to control articulation of the hood 12 and the distal steerable section 264 but also used to further control articulation of the proximal steerable section 262. As shown in the perspective view of FIG. 23A, proximal section control 278 may be actuated, e.g., by rotating the control 278 in a first direction 300, to articulate the proximal steerable section 262 within a first plane, e.g., to retroflex hood 12 and distal steerable section 264 in a corresponding direction of articulation 302. Hood 12 may be further articulated by manipulating steering ring 270, e.g., in a direction of actuation 304, such that distal steerable section 264 moves in a corresponding direction of articulation 306, as shown in FIG. 23B. In one variation, proximal steerable section 262 may be configured to articulate via proximal section control 278 within a single plane while distal steerable section 264 may be configured to articulate in at least four directions, as above. However, both the proximal section control 278 and the steering ring 270 can be manipulated in varying degrees to steer the respective steerable sections to varying curvatures as desired by the operator.

Figure 24:
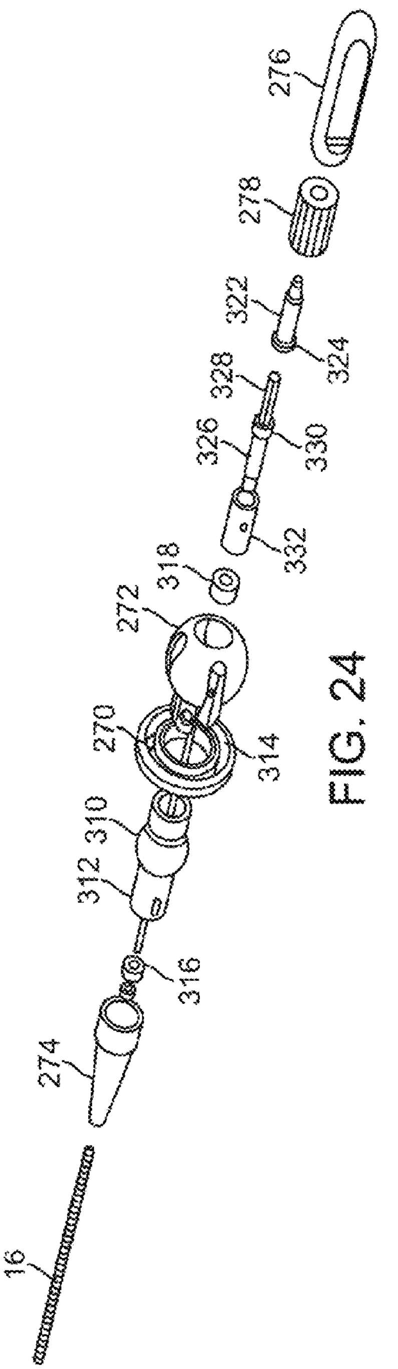
FIG. 24 shows a perspective exploded assembly view of the catheter control handle.
Figure 25:
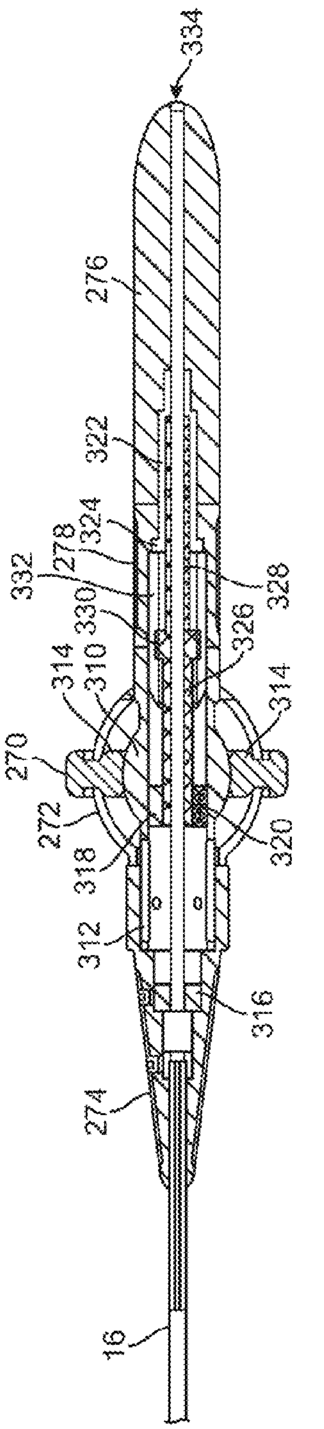
FIG. 25 shows a cross-sectional side view of the catheter control handle.

FIG. 24 shows a perspective exploded assembly view of the handle assembly 260 while FIG. 25 shows a cross-sectional side view of the same handle assembled. As shown, a ball pivot 310 having a pivot support 312 may be supported within a proximal portion of distal handle portion 274. One or more steering ring support members 314 may extend through respective openings defined through housing 272 to support the circumferentially encircling steering ring 270. As above, a pullwire transition manifold 316 may be positioned proximal to the catheter 16 entrance.

A guide shaft 322 may be positioned at least partially through proximal handle portion 276 while maintained in position by retaining lip 324. A sliding shaft portion 328 may be positioned slidably within guide shaft 322 while a distal shaft portion 326 may extend distally through housing 272. A pullwire retaining member 318 having a pullwire termination crimp 320 may be positioned along a distal end of distal shaft portion 326 such that as distal shaft portion 326 is translated distally and/or proximally according to the manipulation of section control 278, the pullwire for the proximal steerable section 262 may be accordingly pulled or pushed. The distal shaft portion 326 may further have a threaded guide 330 which is engaged to a threaded inner surface of retaining sleeve 332, which is secured to section control 278. Thus, as control 278 is rotated, retaining sleeve 332 is also rotated thereby urging distal shaft portion 326 and sliding shaft portion 328 to move accordingly via the engagement with threaded guide 330. A further access lumen 334 is illustrated as extending through the handle assembly 260.

Figure 26:
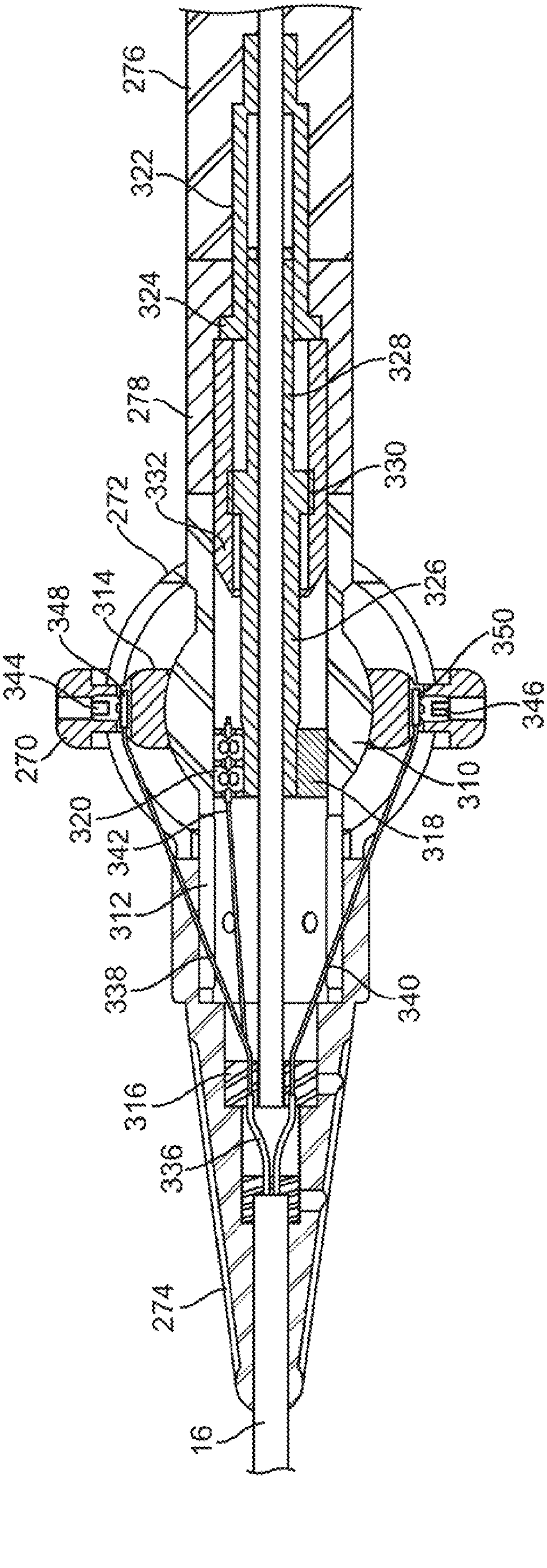
FIG. 26 shows a cross-sectional detail side view of the catheter control handle having the pullwires in place for controlling both the distal and proximal portions.

As further illustrated in the cross-sectional side view of FIG. 26, the one or more proximal steerable section pullwire 342 is shown as extending from catheter 16 and extending through transition manifold 316 and terminated at pullwire retaining member 318. Additionally, one or more distal steerable section pullwires 338, 340 are also shown to emerge from catheter 16, through one or more corresponding compression coils 336, and through transition manifold 316 to terminate at corresponding pullwire termination crimps 348, 350, which may be secured to steering ring 270 via fasteners 344, 346, e.g., set screws. The distal ends these pullwires, e.g., at least four pullwires, can be anchored to the inner walls of the distal steerable section 264. At both the proximal as well as the distal ends, the pullwires may be separated, e.g., by 90°, such that the four-way steerable section is able to be steered symmetrically in at least four directions.

The ends of the compression coils 336 may be glue jointed to the proximal end to the catheter body 16 and distally into the transition manifold 316. Alternatively, the pullwires may also be passed through hypodermic tubes and anchored at the distal side wall of the catheter shaft 16 and the transition manifold 316. Moreover, the pullwires may be made from materials such as stainless steel or nitinol and flexible thin wall compression coils, such as stainless steel coils, may be further slid over each pullwire along the catheter shaft 16.

Figure 27A:
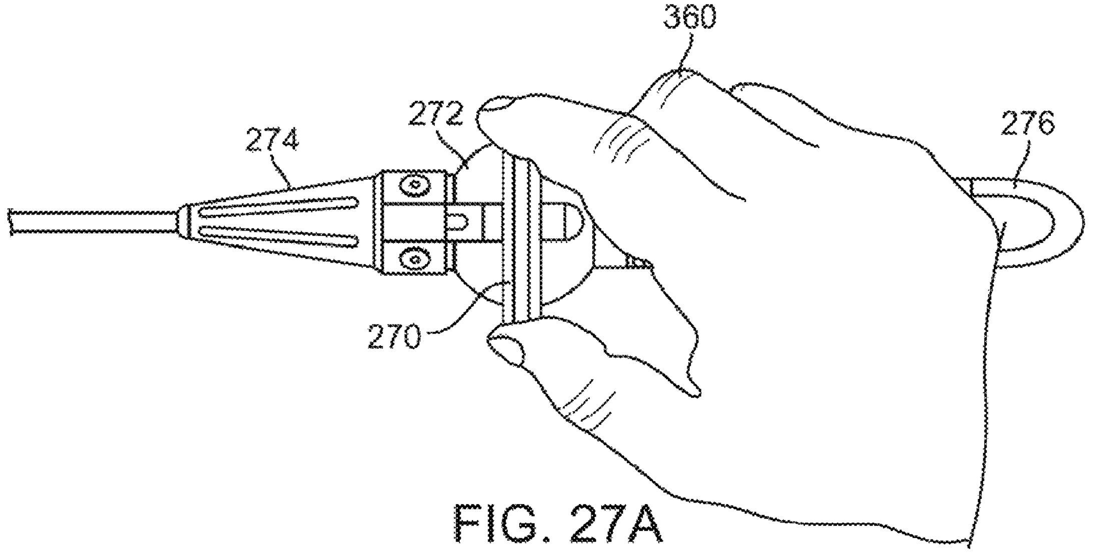
FIGS. 27A and 27B show side views of the control handle under single-handed manipulation whether by a user's right hand or left hand, respectively.
Figure 27B:
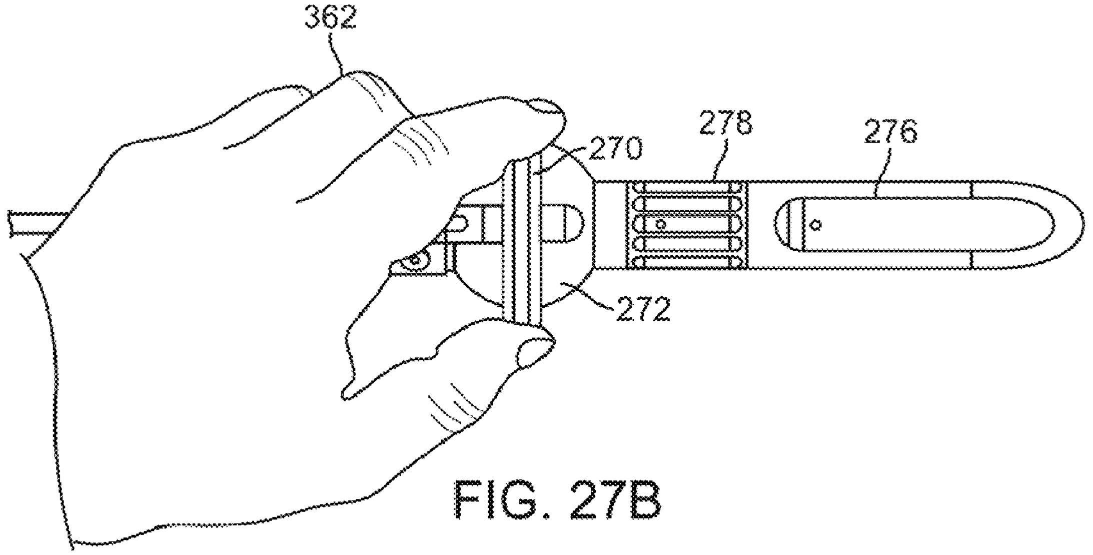

Because of the design of the handle assembly 260 and the accessibility of the steering ring 270 to the user, the user may utilize a single hand to operate the handle assembly 260 to control and manipulate the catheter 16 and hood 12 configuration and position within the patient's body. Moreover, the operator may utilize either their right hand 360, e.g., by gripping handle portion 276, or their left hand 362, e.g., by gripping distal handle portion 274, as shown respectively in FIGS. 27A and 27B.

Figure 28:
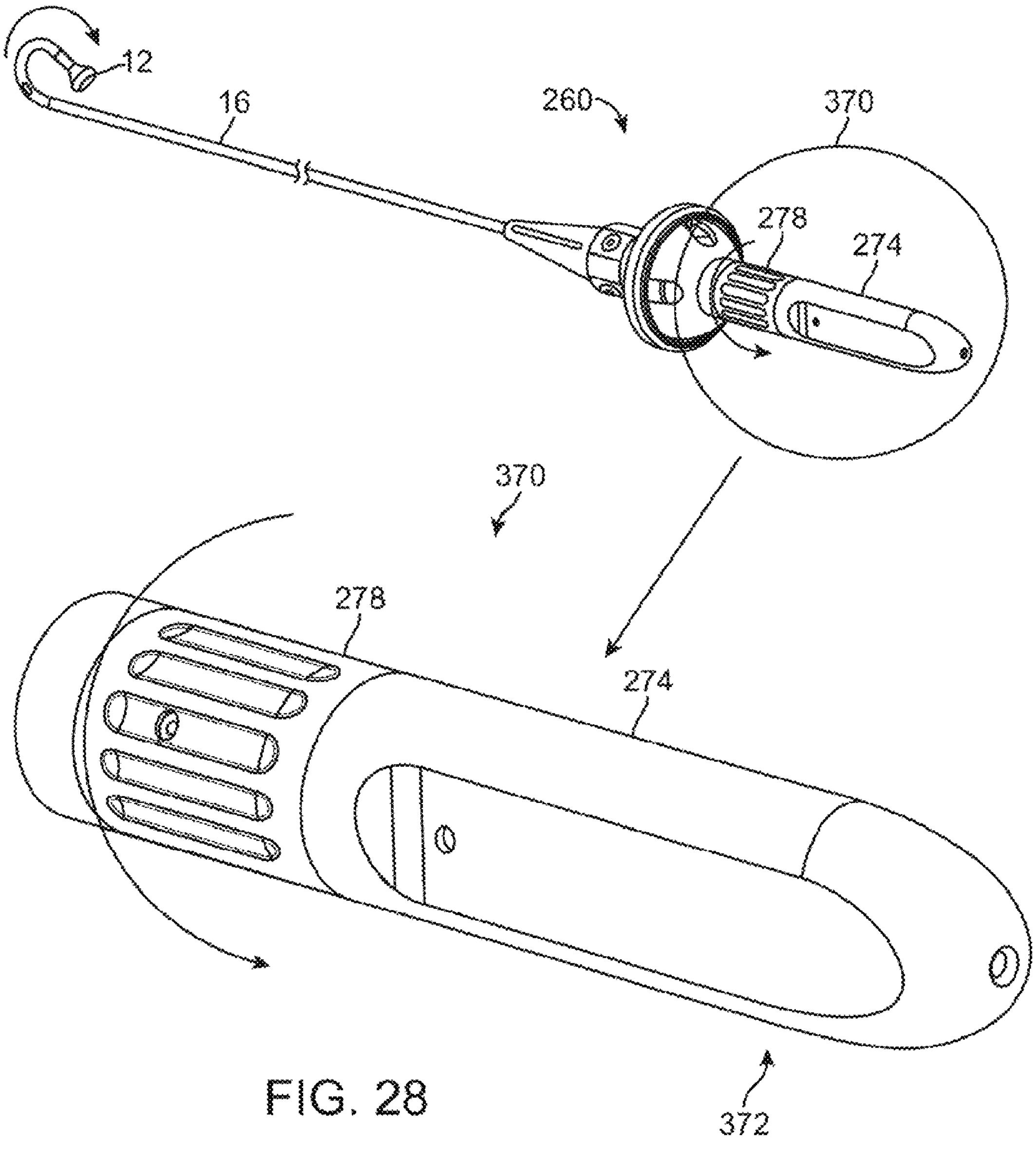
FIG. 28 shows a perspective view of the control handle having an orientation guide located on the handle for reference to the user.

As previously described, because the catheter 16 and hood 12 may be repeatedly torqued and repositioned within the patient's body during a procedure, keeping track of the orientation of the deflection of the hood 12 can be difficult, if not impossible, unless fluoroscopy is used. As the handle assembly 260 provides an indication, as described herein, as to which direction the catheter and hood may be configured based upon the handle orientation, an orientation guide 372 may be imprinted directly upon the handle 274, as shown in detail view 370 of FIG. 28. The plane within which the orientation guide 372 lies may be configured to be parallel to the plane within which the proximal steerable section 262 articulates when section control 278 is manipulated such that the operator may be able to predict how the catheter 16 will configure when manipulated.

Figure 29B:
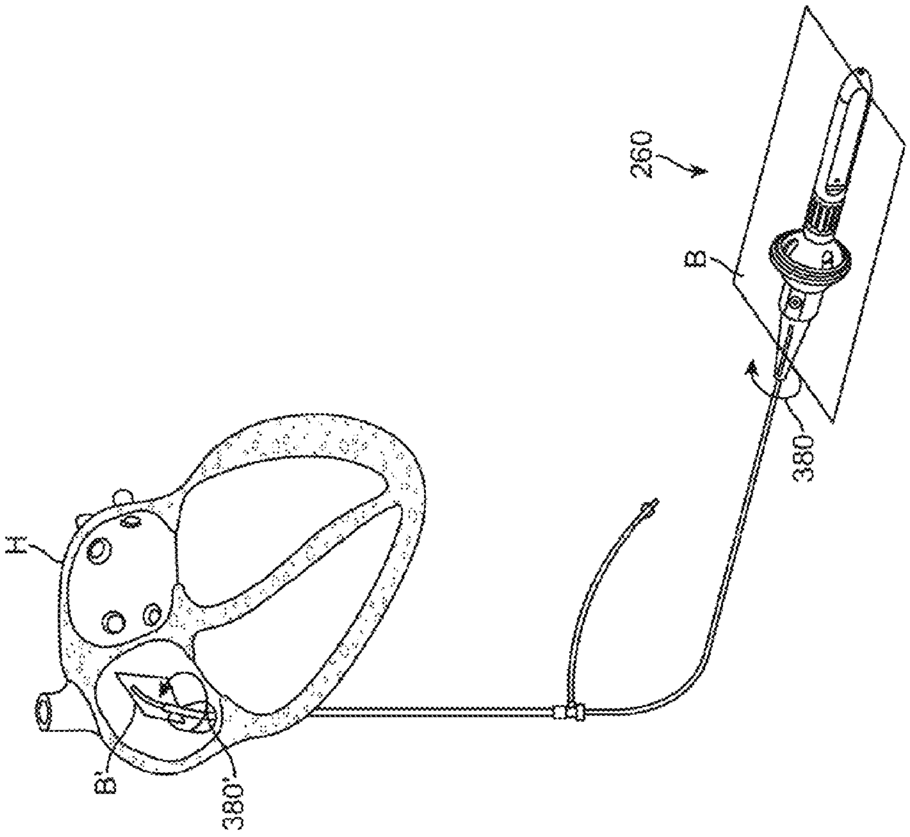
FIGS. 29A and 29B show another example where a visualization hood has been advanced intravascularly within a patient's heart with the control handle positioned external to the patient and illustrates how re-orienting the handle, e.g., by 90°, results in a corresponding articulation of the plane defined by the visualization hood and distal section within the heart.
Figure 29A:
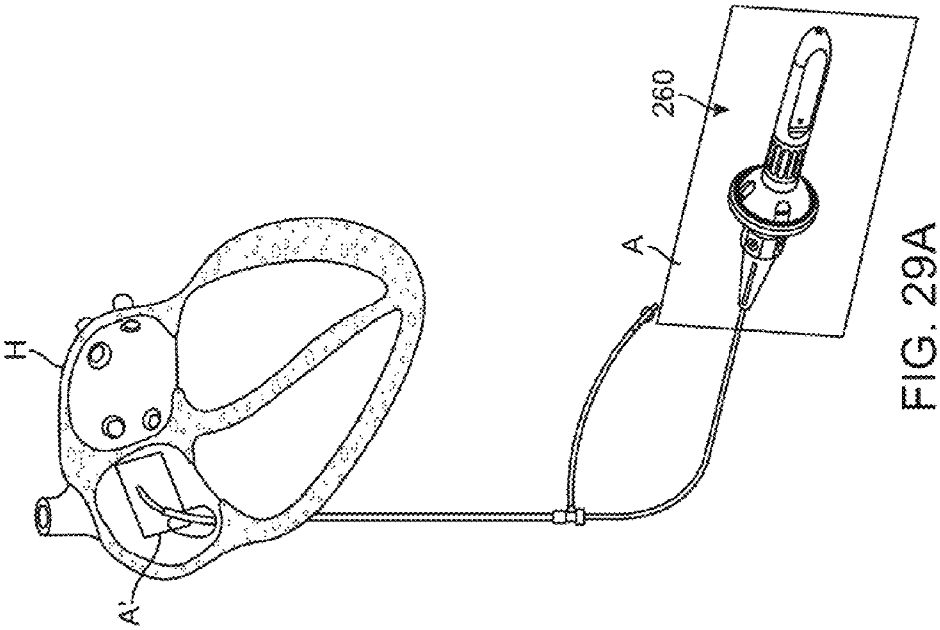

As similarly described above, FIGS. 29A and 29B illustrate a hood positioned within the right atrium of a heart H while coupled to handle assembly 260 positioned external to the body. Handle assembly 260 may be seen as being positioned along plane A while hood 12 and the distal portion of catheter 16 is positioned within corresponding plane A'. As handle assembly 260 is rotated, e.g., at 90°, about its longitudinal axis in a direction of rotation 380 such that handle assembly 260 then lies within a different plane B, hood 12 and the distal steerable portion may also rotate, e.g., at 90°, within the right atrium in a corresponding direction of rotation 380' such that the hood and catheter then define a corresponding different plane B'. Thus, by merely articulating the handle assembly 260 external to the body in a specified direction, the user may adjust or desirably position or re-position the hood within the body in a known direction without having to utilize additional catheter positioning mechanisms.

Figure 30B:
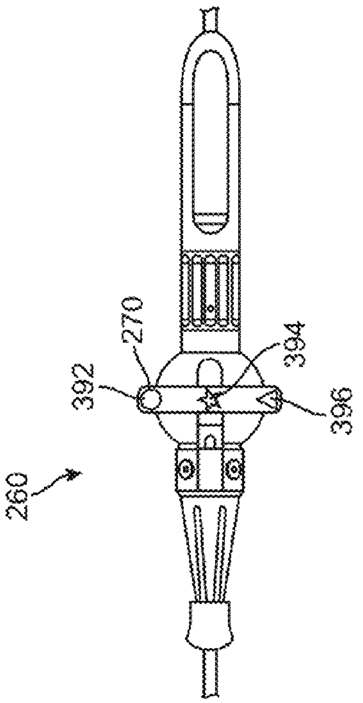
FIGS. 30A and 30B show an end view of the hood from the perspective of an imager positioned within the hood and a side view of the control handle having orientation markers on the steering ring which correspond to similar orientation marks positioned along the hood.
Figure 30A:
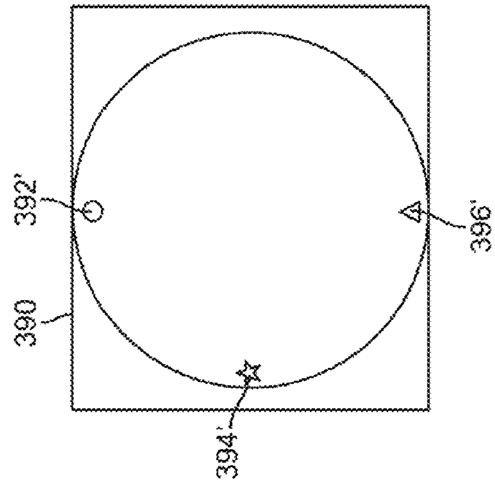

Additionally and/or alternatively, visual indicators positioned directly upon the hood 12 may also be utilized in coordination with corresponding visual indicators positioned upon the handle itself. The hood 12 may have one or more visual indicators marked upon the distal portion of the hood such that the visual image 390 through the hood may show at least a first directional indicator 392' along a first portion of the hood, as shown in FIG. 30A. In this example, a second directional indicator 394' and yet a third corresponding third indicator 396' may be positioned about a circumference of the hood or hood membrane to represent any number of directions. Handle assembly 260 may thus have one or more directional indicators located directly upon, e.g., steering ring 270, which correspond spatially with the indicators positioned upon the hood or hood membrane, as shown in FIG. 30B. For instance, first directional indicator 392' on the hood may correspond spatially with first directional indicator 392 on steering ring 270, second directional indicator 394 on the hood may correspond spatially with second directional indicator 394' on steering ring 270, third directional indicator 396 on the hood may correspond with third directional indicator 396' on steering ring 270, and so on. Although three directional indicators are shown in this example, fewer than three or more than three may be utilized. Moreover, the location and positioning of the indicators may also be varied, as desired.

Figure 30C:
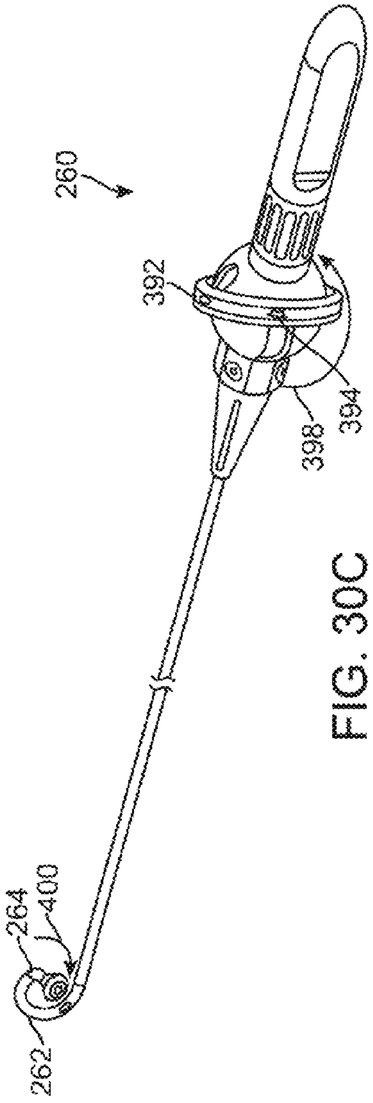
FIG. 30C shows a perspective view illustrating how manipulation of the steering ring in the direction of a particular marker results in a corresponding movement of the visualization hood in a direction as correlated to the marker indicated on the hood.

In use, the directional indicators as viewed through the hood correspond to the direction the hood may move when the steering ring 270 is deflected along the position where the corresponding indicator is located. Thus, deflecting steering ring 270 in direction of actuation 398, e.g., along directional indicator 394, may articulate distal steerable section 264 and hood 12 in a corresponding direction of articulation 400 along the directional indicator 394' shown on the hood or hood membrane, as shown in FIG. 30C. This removes complexity in steering the hood 12, e.g., when the hood 12 is in a retroflexed position, where directions are reversed with respect to the operator.

Figure 31:
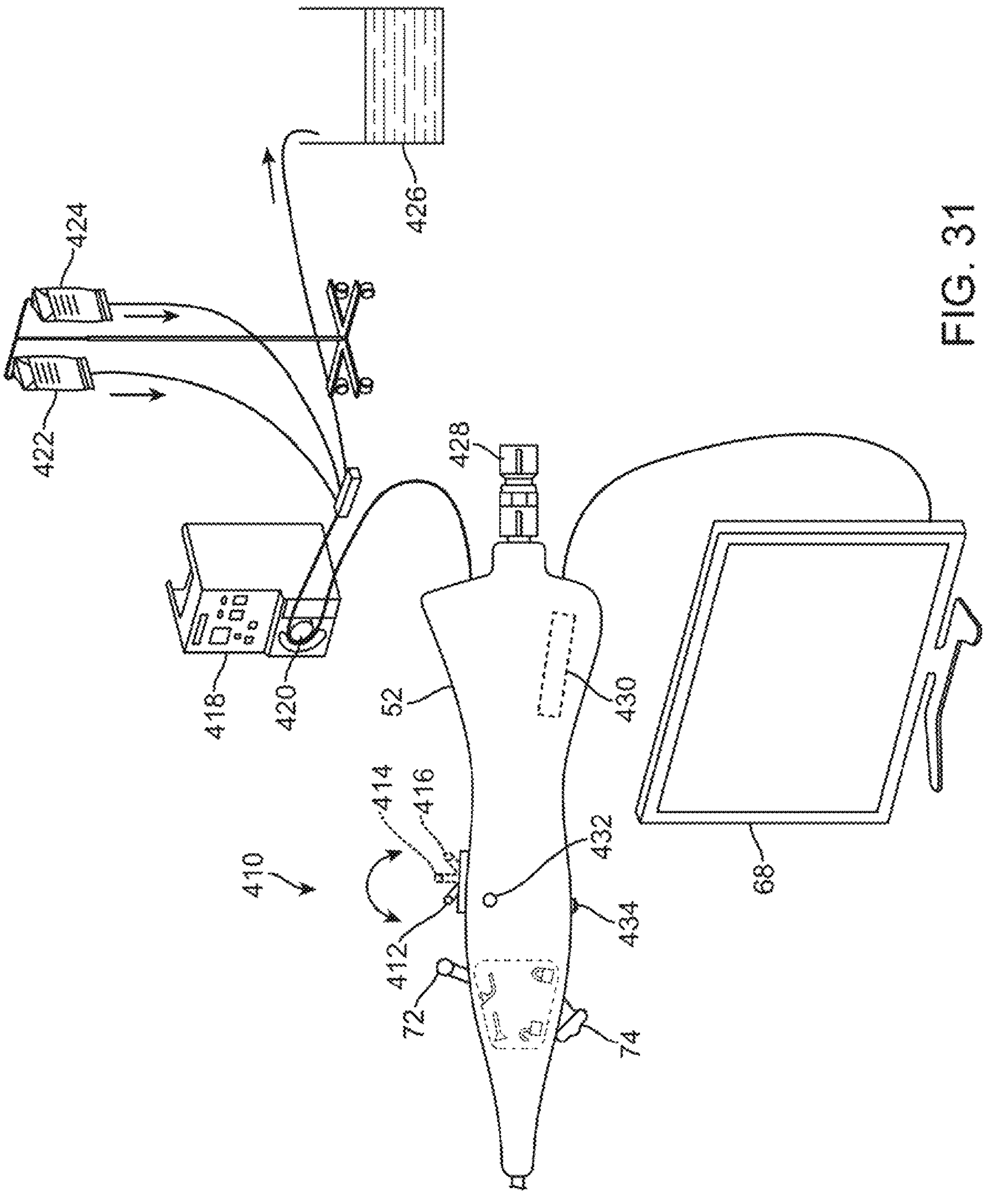
FIG. 31 shows an assembly view of yet another variation of the control handle incorporating multiple features.

The catheter control systems described herein may additionally integrate any number of features and controls for facilitate procedures. These features and controls may be integrated into any of the variations described herein. FIG. 31 shows one example where features such as flow rate control, air bubble detection, ablation activation switches, built-in image sensors, etc., may be incorporated into the handle assembly.

As shown on handle 52, a flow control 410 switch may be incorporated which may optionally have a high-flow position 412, a no-flow position 414, and an optional suction position 416 to control the inflow and/or outflow of the visualization and/or ablation fluid. One or more fluid reservoirs, e.g., a room temperature purging fluid reservoir 422 and/or a chilled purging fluid reservoir 424, may be fluidly coupled to a processing unit 418 which may control various parameters, e.g., valves, inflow, suction, RF ablation energy generation, bubble detection, etc. Processing unit 418 may also incorporate a pump 420, e.g., peristaltic pump, which may pump or urge the fluids from the reservoir through one or more coupling lines into and/or out from handle 52. Processing unit 418 may also be electrically coupled to handle 52 and may also be able to process, display and store several data, including total amount of saline used for the entire procedure, power and duration of ablation, impedance of tissue in contact with hood, rate of flow of saline, temperature of saline, and time of detection of air bubbles during the procedure.

In the event that handle 52 is used to suction or evacuate fluids out from the body, an additional evacuation reservoir 426 may also be fluidly coupled to handle 52. Additionally, one or more hemostasis valves 428 may also be integrated directly upon handle 52. Moreover, an imaging sensor 430 which may also incorporate a light source, e.g., LEDs, and power supply, may additionally be integrated directly into handle 52. A video cable may be connected to the proximal end of the handle 52 and can be directly plugged into any standard video display monitors (such as ones accepting S-Video, DVI, VGA, RCA inputs), rather than utilizing a separate video processing unit.

As processing unit 418 may incorporate processors for detecting various physiological parameters, one or more detection indicators 432, e.g., for bubble detection, and/or ablation actuation switch 434 may be integrated directly upon the handle 52 as an indicator to the operator. If air bubbles are detected in the irrigation channel, the detection indicator 432 may be activated to alert the operator of air bubbles. A soft alarm may also be triggered to further alert the operator. Additionally, with an ablation actuation switch 434 located directly upon handle 52, the operator may be able to instantaneously activate or stop ablation energy from being delivered to the target tissue by depressing switch 434 rather than reaching for a separate ablation generator. Details for tissue ablation under direct visualization and detecting various parameters such as bubble formation are also shown and described in further detail in U.S. patent application Ser. No. 12/118,439 filed May 9, 2008 (U.S. Pat. Pub, 2009/0030412 A1), which is incorporated herein by reference in its entirety.

Figure 32:
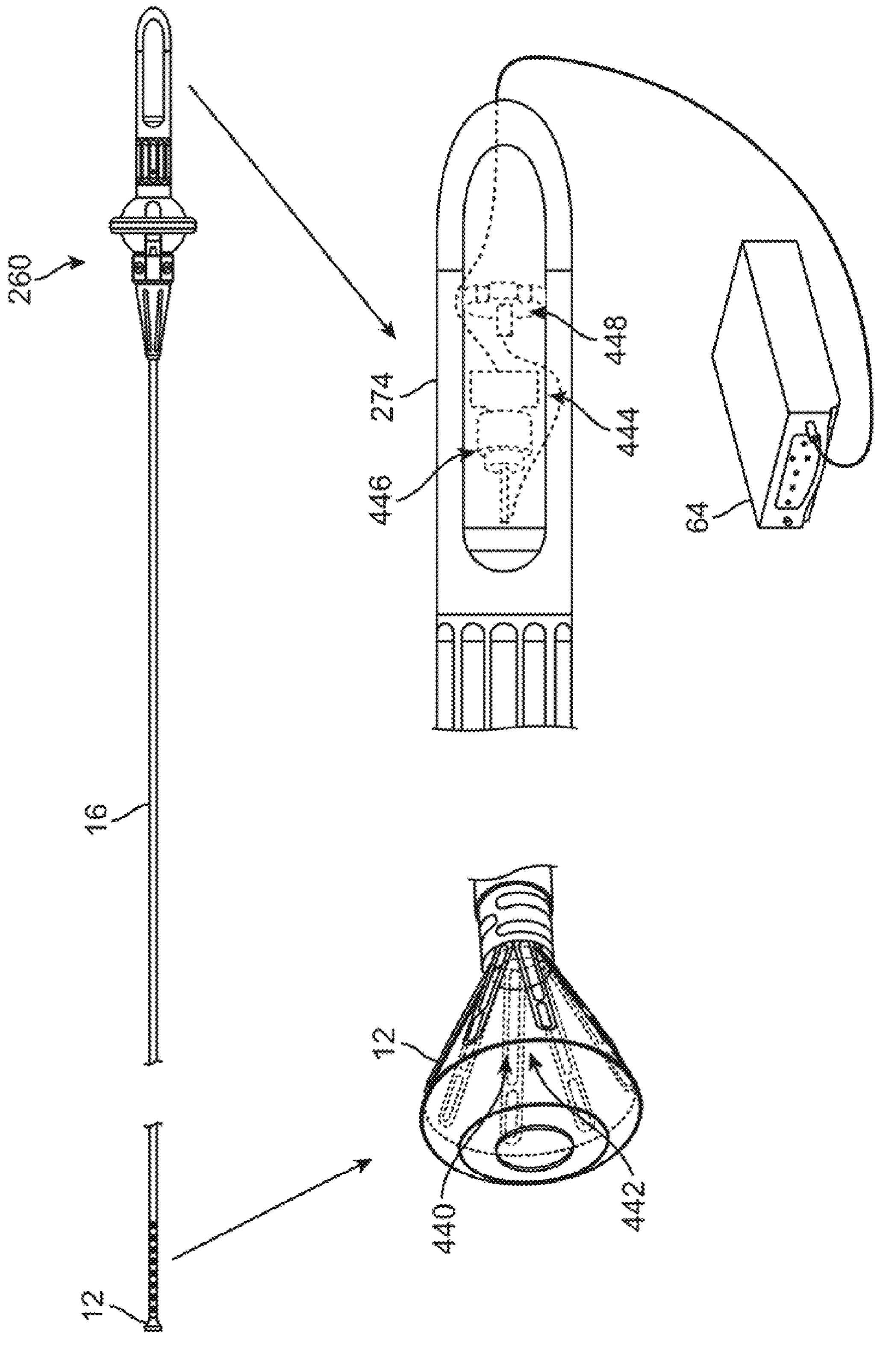
FIG. 32 shows an assembly view of how an imaging system may be incorporated directly within the control handle.

Another example of an integrated handle is shown illustratively in FIG. 32. In this example, handle 274 may incorporate an imaging system directly into the handle. As illustrated, the images captured by the imager 440 positioned within or along hood 12 may be focused onto an electronic imaging sensor 444, e.g., CMOS sensor, positioned within handle 274. Imaging sensor 444 may deliver the images directly to the video processor. A light source 448, e.g., LED light source, may also be placed within the handle 274 to deliver light through, e.g., an optical fiber 442 positioned within hood 12, to illuminate the tissue region to be visualized. At the terminal end of the fiber bundle, a focus lens 446, e.g., a combination of spherical lenses, may be positioned proximal to the fiber bundle. An alternative may utilize a GRIN lens which may be used as a simple one piece element which is chromatically aberration corrected and polarization preserved to allow for more design flexibility. Moreover, a GRIN lens is typically more economical than the spherical lenses.

The applications of the disclosed invention discussed above are not limited to certain treatments or regions of the body, but may include any number of other applications as well. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A medical manipulation assembly comprising:

a catheter including an elongated distal steerable portion with a distal working channel extending through the distal steerable portion and an elongated proximal steerable portion proximal of the distal steerable portion with a proximal working channel extending through the proximal steerable portion, the distal steerable portion and the proximal steerable portion extending along a longitudinal axis of the catheter, wherein the distal and proximal working channels are in fluid communication with one another and are configured to receive an instrument and wherein the distal steerable portion has an outer diameter equal to an outer diameter of the proximal steerable portion;

a distal steering mechanism operable to bend the distal steerable portion in a first plane relative to the proximal steerable portion in response to movement of a first portion of the distal steering mechanism about a first axis of rotation and to bend the distal steerable portion in a second plane relative to the proximal steerable portion in response to movement of a second portion of the distal steering mechanism about a second axis of rotation different than the first axis of rotation;

a proximal steering mechanism operable to bend the proximal steerable portion by rotational movement of the proximal steering mechanism without movement of the first axis of rotation or the second axis of rotation of the distal steering mechanism;

one or more distal pullwires extending between the distal steerable portion and the distal steering mechanism, wherein the distal steering mechanism is mechanically coupled to the one or more distal pullwires; and one or more proximal pullwires extending between the proximal steerable portion and the proximal steering mechanism.

2. The medical manipulation assembly of claim 1 wherein the first axis of rotation is orthogonal to the second axis of rotation.

3. The medical manipulation assembly of claim 1 further comprising the instrument, wherein the instrument is extendable distally beyond the proximal and distal steerable portions.

4. The medical manipulation assembly of claim 3 wherein the instrument comprises a camera.

5. The medical manipulation assembly of claim 3 wherein the instrument comprises a needle.

6. The medical manipulation assembly of claim 1 wherein at least one of the proximal or distal steering mechanisms is operable by computer control.

7. The medical manipulation assembly of claim 1 wherein the distal and proximal working channels are configured for passage of an irrigation fluid therethrough.

8. The medical manipulation assembly of claim 1 wherein the instrument comprises an ablation instrument.

9. The medical manipulation assembly of claim 1 further comprising a lighting source extending within the distal steerable portion.

10. The medical manipulation assembly of claim 1 wherein the one or more proximal and distal pullwires include a compression coil.

11. A method performed by a computing system, the method comprising:

rotating a first portion of a distal steering mechanism about a first axis of rotation to bend an elongated distal steerable portion of a catheter, the distal steerable portion including a distal working channel;

rotating a second portion of the distal steering mechanism about a second axis of rotation different than the first axis of rotation to bend the distal steerable portion;

rotating a proximal steering mechanism independently of the rotating of the first or second portions of the distal steering mechanism, to bend an elongated proximal steerable portion of the catheter, the proximal steerable portion extending proximally of the distal steerable portion and including a proximal working channel, the distal steerable portion and the proximal steerable portion extending along a longitudinal axis of the catheter, wherein the distal and proximal working channels are in fluid communication with one another and are configured to receive an instrument and wherein the distal steerable portion has an outer diameter equal to an outer diameter of the proximal steerable portion;

responsive to the rotating of the first portion of the distal steering mechanism, manipulating one or more distal pullwires extending between the distal steerable portion and the distal steering mechanism to bend the distal steerable portion in a first plane relative to the proximal steerable portion, wherein the distal steering mechanism is mechanically coupled to the one or more distal pullwires;

responsive to the rotating of the second portion of the distal steering mechanism, manipulating the one or more distal pullwires to bend the distal steerable portion in a second plane relative to the proximal steerable portion; and responsive to the rotating of the proximal steering mechanism, manipulating one or more proximal pullwires extending between the proximal steerable portion and the proximal steering mechanism to bend the proximal steerable portion.

12. The method of claim 11 wherein the first axis of rotation is orthogonal to the second axis of rotation.

13. The method of claim 11 further comprising extending the instrument distally beyond the proximal and distal steerable portions.

14. The method of claim 11 wherein the instrument comprises a camera.

15. The method of claim 11 wherein the instrument comprises a needle.

16. The method of claim 11 further comprising displaying an image obtained by the instrument.

17. The method of claim 11 further comprising conveying an irrigation fluid through the distal and proximal working channels.

18. The method of claim 11 further comprising receiving the instrument through the distal and proximal working channels, wherein the instrument comprises an ablation instrument.

19. The method of claim 11 further comprising operating a lighting source positioned within the distal steerable portion.

20. The method of claim 11 wherein the one or more proximal and distal pullwires include a compression coil.

* * * * *